(12) United States Patent
Carpenter et al.

(10) Patent No.: US 11,690,564 B2
(45) Date of Patent: Jul. 4, 2023

(54) TRAINING PLANS AND WORKOUT COACHING FOR ACTIVITY TRACKING SYSTEM

(71) Applicant: MYFITNESSPAL, INC., San Francisco, CA (US)

(72) Inventors: Kaitlyn Carpenter, Austin, TX (US); Jeff Knight, Austin, TX (US); Luke Montzingo, Austin, TX (US); Daniel Townson, Austin, TX (US); Jonathan Laas, Austin, TX (US); Pedro Feitosa, Austin, TX (US); Bradford J. Fults, Austin, TX (US)

(73) Assignee: MyFitnessPal, Inc., Austin, TX (US)

( * ) Notice: Subject to any disclaimer, the term of this patent is extended or adjusted under 35 U.S.C. 154(b) by 717 days.

(21) Appl. No.: 16/691,849

(22) Filed: Nov. 22, 2019

(65) Prior Publication Data

US 2021/0153805 A1 May 27, 2021

(51) Int. Cl.
*A61B 5/00* (2006.01)
*A61B 5/11* (2006.01)
(Continued)

(52) U.S. Cl.
CPC .............. *A61B 5/486* (2013.01); *A61B 5/002* (2013.01); *A61B 5/112* (2013.01); *A61B 5/1118* (2013.01);
(Continued)

(58) Field of Classification Search
CPC ....... A61B 5/486; A61B 5/1118; A61B 5/112; A61B 5/6807; A61B 5/681; A61B 5/6898;
(Continued)

(56) References Cited

U.S. PATENT DOCUMENTS 10,258,288 B2 4/2019 Penders
10,300,334 B1 * 5/2019 Chuang .............. A63B 24/0062
(Continued)

OTHER PUBLICATIONS

Unpublished U.S. Appl. No. 16/696,232 to Carpenter et al., filed Nov. 26, 2019.
(Continued)

*Primary Examiner* — Jay Trent Liddle
*Assistant Examiner* — Alyssa N Brandley
(74) *Attorney, Agent, or Firm* — Maginot, Moore & Beck, LLP

(57) ABSTRACT

A method of providing workout training for a user of an activity tracking system includes displaying a plurality of training plan options to the user on a screen of a personal electronic device, and then receiving a selected training plan option from the user. Selected workout day options are received from the user and the system generates a training schedule for the user based on the selected training plan and the selected workout day options. One or more reminders identify the type of workout for the scheduled day and an option to accept or reject the workout. When the user selects the option to accept the workout, the workout goal associated with the scheduled workout is displayed. The method further includes determining progress toward the workout goal based on the received workout data, and displaying an indicator of progress toward the workout goal on the screen during the workout.

18 Claims, 13 Drawing Sheets

(51) Int. Cl.
*A63B 24/00* (2006.01)
*A63B 69/00* (2006.01)
*A63B 71/06* (2006.01)

(52) U.S. Cl.
CPC ............ *A61B 5/681* (2013.01); *A61B 5/6807* (2013.01); *A61B 5/6898* (2013.01); *A61B 5/744* (2013.01); *A63B 24/0075* (2013.01); *A63B 69/0028* (2013.01); *A63B 71/0622* (2013.01); *A63B 71/0686* (2013.01); *A63B 2024/0068* (2013.01); *A63B 2071/0663* (2013.01); *A63B 2071/0694* (2013.01); *A63B 2220/836* (2013.01); *A63B 2225/50* (2013.01)

(58) Field of Classification Search
CPC . A61B 5/744; A63B 24/0075; A63B 69/0028; A63B 71/0622; A63B 71/0686; A63B 2024/0068; A63B 2071/0663; A63B 2071/0694; A63B 2220/836
See application file for complete search history.

(56) References Cited

U.S. PATENT DOCUMENTS

| | | | |
|---|---|---|---|
| 10,878,952 B1 | 12/2020 | Patel et al. | |
| 11,056,238 B1 | 7/2021 | Nakajima | |
| 11,062,591 B1 | 7/2021 | Cascioli | |
| 11,151,888 B1 | 10/2021 | Fillinger | |
| 11,217,341 B2 | 1/2022 | Hope | |
| 11,217,343 B2 | 1/2022 | Lee | |
| 2007/0011919 A1 | 1/2007 | Case | |
| 2008/0096726 A1* | 4/2008 | Riley | A61B 5/1118 482/8 |
| 2009/0047645 A1* | 2/2009 | Dibenedetto | A61B 5/0002 434/258 |
| 2009/0048070 A1* | 2/2009 | Vincent | H04B 1/385 482/8 |
| 2011/0214030 A1 | 9/2011 | Greenberg et al. | |
| 2012/0274508 A1* | 11/2012 | Brown | A63B 24/0062 342/357.57 |
| 2014/0107932 A1 | 4/2014 | Luna | |
| 2014/0200691 A1* | 7/2014 | Lee | A63B 24/0062 700/91 |
| 2014/0343380 A1 | 11/2014 | Carter et al. | |
| 2014/0350883 A1 | 11/2014 | Carter et al. | |
| 2015/0281364 A1 | 10/2015 | Connolly | |
| 2015/0358767 A1 | 12/2015 | Luna et al. | |
| 2017/0020444 A1 | 1/2017 | Lurie | |
| 2018/0042542 A1 | 2/2018 | Cronn et al. | |
| 2018/0114124 A1 | 4/2018 | Cronn et al. | |
| 2018/0336530 A1* | 11/2018 | Johnson | G06Q 10/1093 |
| 2019/0105535 A1 | 4/2019 | Kovach et al. | |
| 2019/0254522 A1 | 8/2019 | Brancaccio et al. | |
| 2019/0266505 A1* | 8/2019 | Gindre | G06Q 10/04 |
| 2020/0005928 A1 | 1/2020 | Daniel | |
| 2020/0016457 A1 | 1/2020 | Ben-Chanoch et al. | |
| 2020/0075152 A1 | 3/2020 | Radovcic | |
| 2020/0075167 A1 | 3/2020 | Srivastava et al. | |
| 2020/0100704 A1* | 4/2020 | Salehian | A61B 5/1112 |
| 2020/0105404 A1 | 4/2020 | Major et al. | |
| 2020/0113518 A1 | 4/2020 | Mollohan | |
| 2020/0160961 A1 | 5/2020 | Wadhawan et al. | |
| 2020/0167815 A1 | 5/2020 | Naik et al. | |
| 2020/0211410 A1 | 7/2020 | De Magalhaes et al. | |
| 2020/0250508 A1 | 8/2020 | De Magalhaes et al. | |
| 2020/0275394 A1 | 8/2020 | Lam et al. | |
| 2020/0297269 A1 | 9/2020 | Vieri | |
| 2020/0405158 A1 | 12/2020 | Jeong et al. | |
| 2021/0026440 A1 | 1/2021 | Poupyrev et al. | |
| 2021/0041159 A1 | 2/2021 | Uchida et al. | |
| 2021/0043301 A1 | 2/2021 | Goel et al. | |
| 2021/0093919 A1 | 4/2021 | Lyke et al. | |
| 2021/0125728 A1 | 4/2021 | Dessaud et al. | |
| 2021/0146195 A1 | 5/2021 | Szpiczynski | |
| 2021/0154530 A1 | 5/2021 | Carpenter et al. | |
| 2021/0174971 A1 | 6/2021 | Jain et al. | |
| 2021/0236025 A1 | 8/2021 | Comtois et al. | |
| 2021/0241649 A1 | 8/2021 | Kinnunen | |
| 2021/0330211 A1 | 10/2021 | Han et al. | |
| 2022/0022778 A1 | 1/2022 | Gauthier | |

OTHER PUBLICATIONS

Garmin, Image of three watches with graphical user interface, available on or before Jul. 31, 2019, (npl_ref1_Garmin_1).
Garmin, Image of watch with graphical user interface, available on or before Jul. 31, 2019, (npl_ref2_Garmin_2).
Polar, Image of watch with graphical user interface, available on or before Jul. 31, 2019, (npl_ref3_Polar).
Suunto, Image of watch with graphical user interface, available on or before Jul. 31, 2019, (npl_ref4_Suunto_1).
Suunto, Image of two watches with graphical user interface, available on or before Jul. 31, 2019, (npl_ref5_Suunto_2).
Suunto, Image of watch with graphical user interface, available on or before Jul. 31, 2019, (npl_ref6_Suunto_3).
Suunto, Image of watch with graphical user interface, available on or before Jul. 31, 2019, (npl_ref7_Suunto_4).

* cited by examiner

TRAINING PLANS AND WORKOUT COACHING FOR ACTIVITY TRACKING SYSTEM

COPYRIGHT

A portion of the disclosure of this patent document contains material that is subject to copyright protection. The copyright owner has no objection to the facsimile reproduction by anyone of the patent document or the patent disclosure, as it appears in the United States Patent and Trademark Office patent files or records, but otherwise reserves all copyright rights whatsoever.

FIELD

The device and method disclosed herein relates to fitness tracking systems and, more particularly, to coaching, training and associated displays provided by such fitness tracking systems.

BACKGROUND

Activity tracking devices are increasingly utilized by individuals interested in tracking metrics related to their personal health and fitness activity. These activity tracking devices include, for example, heart rate monitors, step counters, stair counters, global positioning system ("GPS") tracking devices, as well as various other motion and biometric tracking devices. One of the most popular fitness activities is running. Running is implemented by many individuals for general health and fitness as well as weight loss. Other individuals implement running in a competitive manner, whether against other individuals, or simply striving to meet personal goals. In any event, a common problem for runners is the risk of injury. This is especially true of those just beginning to run or those attempting to train for some event or other purpose. In these situations, it is important that an athlete finds an acceptable level of training without over-training or under training. A proper amount of training, including both distance, time and speed, along with a proper running form (e.g., a proper cadence) is one the best ways for runners to achieve their goals and also minimize the risk of injury. Unfortunately, typical guidelines and other information available to runners falls short of providing runners of all levels, and especially beginning and intermediate-level runners, with the necessary tools to achieve and maintain a proper running form and training amount. Typical guidelines tend to be a one-size-fits-all standard that fails to consider the unique physiological characteristics of the runner and desired goals of the runner. Furthermore, even with appropriate guidelines, it is challenging for users to implement training plans and achieve proper running form. Accordingly, for many runners, the typical guidelines may be difficult to apply and are sometimes counterproductive. In view of the foregoing, it would be advantageous to provide a method of providing training plans for runners that is unique to the individual runner and includes various features that assist the user in achieving their running goals. It would also be advantageous if the method provided the user with specific guidance for how to achieve and maintain a proper running form.

SUMMARY

In accordance with one exemplary embodiment of the disclosures, a method of providing workout training for a user of an activity tracking system is disclosed. The activity tracking system includes an activity sensor configured to send activity data to at least one personal electronic device. The method includes displaying a plurality of training plan options to the user on a screen of the at least one personal electronic device, each of the training plan options associated with a different user goal and including a plurality of different types of workouts to be performed during a training period. The method further includes receiving a selected training plan option from the user via the at least one personal electronic device and displaying workout day options to the user on the screen, each of a first plurality of the workout day options including a day on which the user intends to workout during each week of the training period for the selected training plan. Additionally, the method includes receiving selected workout day options from the user via the at least one personal electronic device and generating a training schedule for the user based on the selected training plan and the selected workout day options, wherein the training schedule includes scheduled workout days, one of the types of workouts for each scheduled workout day, and a workout goal associated with each scheduled workout day. Thereafter, the method includes displaying one or more reminders on the screen of the at least one personal electronic device on one of the scheduled workout days, each of the reminders including an option to accept or reject the workout. When the user selects the option to accept the workout on the scheduled workout day, displaying the workout goal associated with the scheduled workout to the user on the screen of the at least one personal electronic device, receiving workout data from the sensor during the workout, determining progress toward the workout goal based on the received workout data, and displaying an indicator of progress toward the workout goal to the user on the screen during the workout. When the user reaches the workout goal, indicating on the screen that the user has reached the goal for the workout.

In at least one embodiment, an activity tracking system comprises a shoe configured to generate activity data and transmit the activity data, and at least one personal electronic device configured to receive the activity data from the shoe. The at least one personal electronic device includes a memory configured to store the received activity data, a data processor in communication with the memory, and a display in communication with the data processor. The at least one personal electronic device is configured to present a plurality of training plan options to a user via the display of the at least one personal electronic device, each of the training plan options associated with a different user goal and including a plurality of different types of workouts to be performed during a training period. The at least one personal electronic device is further configured to receive a selected training plan option from the user via the display and present workout day options to the user via the display, each of the workout day options including a day of week on which the user intends to workout during the training period for the selected training plan. Additionally, the at least one personal electronic device is configured to receive selected workout day options from the user via the display and generate a training schedule for the user based on the selected training plan and the selected workout day options, wherein the training schedule includes scheduled workout days, one of the types of workouts for each scheduled workout day, and a workout goal associated with each scheduled workout day. Furthermore, the at least one personal electronic device is configure to present one or more reminders to the user on the display on scheduled workout days, each of the reminders identifying the type of workout for the scheduled day and an option to accept or reject the workout. When the user selects the option to accept the workout, the workout goal associated with the scheduled workout is presented to the user on the screen of the at least one personal electronic device. The personal electronic device receives workout data from the shoe during the workout, determines progress toward the workout goal based on the received workout data, and presents the progress toward the workout goal to the user on the screen during the workout. When the user reaches the workout goal, the screen of the personal electronic device indicates that the user has reached the goal for the workout.

In yet another exemplary embodiment, a method is provided for coaching a user of an activity tracking system. The activity tracking system includes a shoe configured to send activity data to at least one personal electronic device. The method includes receiving workout data from the shoe during the workout, the workout data including pace data. The method further includes displaying a segmented bar on a screen of the at least one personal electronic device, the segmented bar including a first portion associated with values for the workout data that are within a target range, a second portion associated with values for the workout data below the target range, and a third portion associated with values for the workout data that are above the target range, wherein a first break separates the first portion of the segmented bar from the second portion of the segmented bar, wherein a second break separates the first portion of the segmented bar from a third portion of the segmented bar, wherein a lower value of the target range is displayed on the screen in proximity of the first break, and wherein an upper value of the target range is displayed on the screen in proximity of the second break. Additionally, the method includes dynamically adjusting the target range and the associated upper value and lower value displayed on the watch face during the workout based on changes in the pace data.

These and other aspects of the disclosure shall become apparent when considered in light of the disclosure provided herein.

BRIEF DESCRIPTION OF THE DRAWINGS

The foregoing aspects and other features of a fitness tracking system are explained in the following description, taken in connection with the accompanying drawings.

FIG. 15 is a front view of the watch of FIG. 13 with the watch face showing the cadence of the user below the target range;

FIG. 16 is a front view of the watch of FIG. 13 with the watch face showing the cadence of the user above the target range;

FIG. 17 is a front view of the watch of FIG. 13 with the watch face showing the cadence target range as a dynamic range based on user pace.

All Figures© Under Armour, Inc. 2019. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

General Arrangement of the Fitness Tracking System

Figure 1:
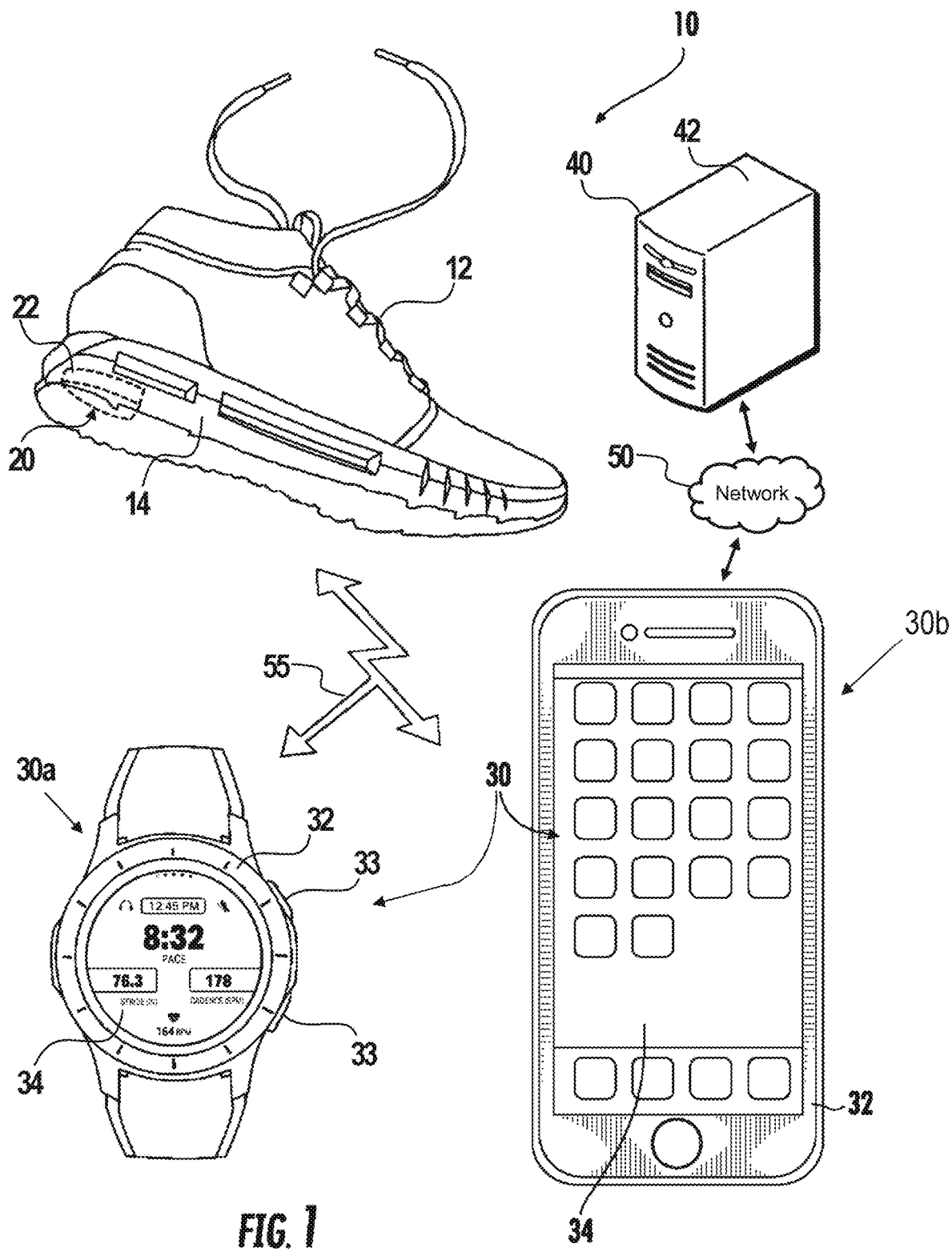
FIG. 1 is a diagrammatic view showing an exemplary embodiment of a fitness tracking system including activity monitoring devices, an electronic display device, and a system server.

With reference to FIG. 1, an exemplary embodiment of a fitness tracking system 10 is shown for recording fitness data during an activity or workout. The fitness tracking system 10 (which may also be referred to herein as the "health tracking system" or the "activity tracking system") includes at least one activity monitoring device 20 provided on fitness equipment, such as a shoe, and at least one electronic display device 30 in communication with the activity monitoring device via a short range wireless network 55. In at least one embodiment, the fitness tracking system 10 further includes a remote system server 40 in communication with the electronic display device 30 via a network 50, such as the Internet. As described herein, a fitness app is provided on the electronic display device. The fitness app is configured to offer training plans to users via a graphical user interface. As described in further detail below, the fitness app also includes a dynamic coaching screen configured to assist users in properly implementing the fitness equipment associated with the activity monitoring device. The dynamic coaching screen includes a multi-segment bar with one segment of the bar providing an adjustable target range dependent at least in part on changes in the pace data during the workout.

The activity monitoring device 20 is a user device configured to measure one or more health and fitness parameters of a user during an activity or workout and provide fitness data regarding the activity or workout to the electronic display device 30. In many embodiments, the activity monitoring device 20 (which may also be referred to herein as an activity "tracking device" and/or "sensor device") is designed and dimensioned to be worn on or carried by or otherwise retained upon the body of a user during a fitness activity, such as a run. In the illustrated embodiment, the activity monitoring device 20 is integrated with fitness equipment, such as a running shoe 12 or other article of footwear. However, in other embodiments, the activity monitoring devices may be designed and dimensioned in other forms, such as to be worn on the wrist, waist or ankle of the user, or integrated into another article of apparel. In some embodiments, the fitness tracking system 10 includes multiple activity monitoring devices associated with the individual user.

The term "fitness data" or as used herein refers to data relating to a user's fitness and performance during an activity or workout, but also data regarding the user's health and general well-being outside of the activity or workout, and may also be referred to herein as "fitness information" or "workout data." Fitness data may include activity data and physiological data. Fitness data may be in a raw measured form or in a processed form. Fitness data may be automatically measured, sensed, or collected by the activity monitoring device 20 and/or the electronic display device 30, but may also be entered manually by the user via the activity monitoring device 20 and/or the electronic display device 30. The term "activity data" as used herein is a subset of fitness data, and refers to data related to physical activity (i.e., movement or lack thereof) of the user. Examples of activity data include body motion/acceleration data, step data, stride length data, stride cadence data, foot strike data, distance traversal data, pace/speed data, altitude data, environmental/positional data (such that provided by a GPS receiver), exercise weight/resistance data, exercise repetition data, and/or any of various other types of personal activity metrics that may be relevant the user's physical activity for a given period of time. The term "physiological data" as used herein is a subset of fitness data, and refers to data related to the physiological status and health of the user. Examples of physiological data include age, gender, height, body weight, body fat, heart rate, aspiration rate, blood oxygenation, blood glucose, hydration, caloric expenditure, or any of various other types of physiological metrics that may be relevant the user's physiological health for a given period of time.

Fitness data collected by the activity monitoring device 20 is transmitted to the electronic display device 30 via a short-range wireless network 55 (e.g., a WiFi network, Bluetooth network, etc.). As shown in FIG. 1, the electronic display device 30 is provided in the form of a smartwatch 30a, smartphone 30b, or other personal electronic device, and is designed to process the fitness data and display such data to the user in a format that summarizes a user's performance during or after an activity or workout. In some embodiments, the electronic display device 30 may also collect fitness data independently of any dedicated activity monitoring device(s) and, in this way, may function as the activity monitoring device or as one of the activity monitoring devices. Accordingly, it will be recognized that in various embodiments the electronic display device 30 and the activity monitoring device 20 may be integrated into a single unit (e.g., a smartphone 30b or a smartwatch 30a may serve as both the electronic display device 30 and the activity monitoring device 20).

While the activity monitoring device 20 is described herein as the primary devices for collecting and transmitting fitness data to the electronic display device 30, it will be recognized that additional data may also be collected or otherwise obtained and/or input into the electronic display device 30 via various other mechanisms. In at least one embodiment, the user may manually input fitness data directly into the electronic display device 30. For example, the user may manually enter physiological data without the use of a sensor and/or other device for transmitting the fitness data to the electronic display device 30.

As noted above, fitness data 24 from the activity monitoring device 20 is delivered wirelessly to the electronic display device 30 and stored in the memory 38. As indicated by the arrow representing the network 55 in FIGS. 1 and 2, the activity monitoring device 20 is configured to transmit a wireless RF signal representative of the fitness data collected or obtained thereat to the electronic display device 30. In addition, the fitness data may also be transmitted to additional personal electronic devices or computing devices, such as a personal computer and/or a laptop computer where the fitness data may be conveniently displayed for the user. In other embodiments, a wired connection may be utilized for communication of fitness data between the electronic display device 30 and the activity monitoring device 20. Similarly, in another embodiment, the fitness data 24 may be transmitted from the activity monitoring device 20 and/or the electronic display device 30 to the system server 40. The data may then be accessed by the user at any number of additional computerized devices via a username and password, or other form of identification and authentication of the user.

Client-side fitness tracking software in the form of a fitness app 31 is also provided on the electronic display device 30. The fitness app 31 is stored within the memory 38 of the electronic display device 30 and is executed by the processor 37. Various features of the fitness app 31 and methods implemented by the fitness app are described in further detail below. In various embodiments, the fitness app 31 is configured to offer training plans to users via a graphical user interface 34. The fitness app 31 also provides a dynamic coaching screen configured to assist users in properly implementing the fitness equipment associated with the activity monitoring device.

The remote system server 40 comprises a computerized device or data processing system configured to run one or more software applications on a processor thereof for storing and processing fitness data. The activity monitoring device 20 and electronic display device 30 may communicate via the network 50/55 to the system server 40 for storage and/or processing of the fitness data, thereby decreasing the processing capacity required at either user device (e.g., the activity monitoring device 20 or electronic display device 30). In at least one embodiment, the remote system server 40 maintains a database of fitness data received from the electronic display device 30 and/or the activity monitoring device 20, as well as fitness data received from further electronic display devices and/or activity monitoring devices associated with a plurality of other users.

In at least one embodiment, the transmission of data from the activity monitoring device 20 to the electronic display device 30 or to the system server 40 occurs automatically without requiring the user to prompt or initiate the transmission. In another embodiment, the activity monitoring device 20 may be configured to begin transmissions once it receives a confirmation that the electronic display device 30 is within an appropriate range of the activity monitoring device 20. In yet another embodiment, data transmission may occur periodically at predetermined intervals of time. In other embodiments, where communications between the activity monitoring device 20 and the electronic display device 30 are made with a wired connection, communications only occur when the wired connection is established between the activity monitoring device 20 and the electronic display device 30. Similar logic applies to the transmission of data from the activity monitoring device 20 and/or the electronic display device 30 to the system server 40. Additional description concerning each of the activity monitoring device 20, the electronic display device 30, and the system server 40 is provided below, after the following description of the methods implemented by such components.

The foregoing describes the general arrangement for an activity tracking system. Methods for operating the fitness tracking system 10 are described below in additional detail. As will be understood in association with the description herein, methods of operating the electronic display device 30 and/or the activity monitoring device 20 provide unique training plans and coaching features for runners and other athletes. In the description of the methods, statements that a method is performing some task or function refers to a controller or general purpose processor executing programmed instructions stored in non-transitory computer readable storage media operatively connected to the controller or processor to manipulate data or to operate one or more components in the fitness tracking system 10 to perform the task or function. Particularly, the processor 37a, 37b of the electronic display device(s) 30a, 30b, the processor 47 of the system server, and/or the processor 27 of the activity monitoring device 20 may be such a controller or processor. Alternatively, the controller or processor may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Pairing Shoes With Display Device

Figure 3:
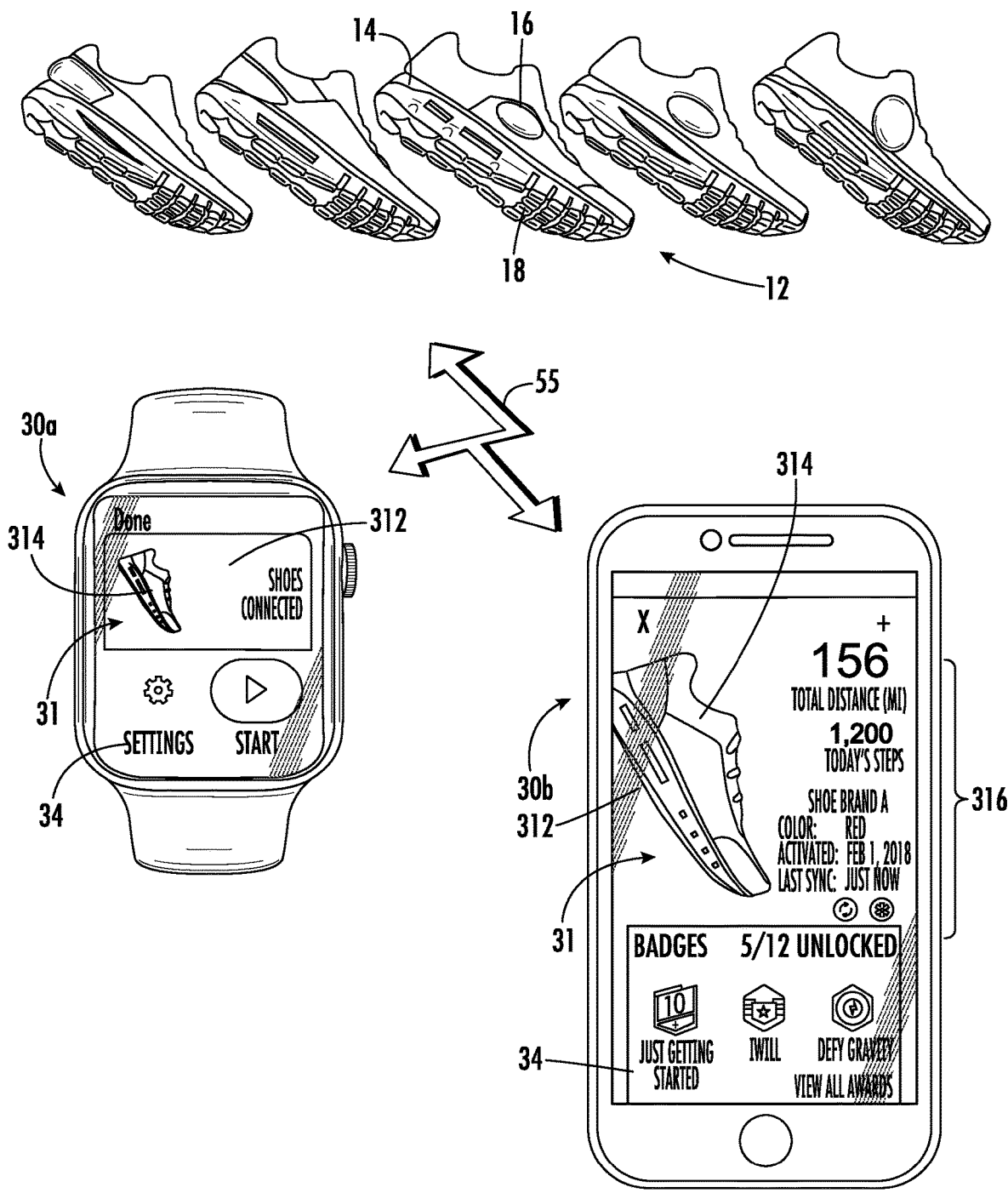
FIG. 3 is a diagrammatic view showing a smart shoe, a smartphone, and a smart watch all paired together within the fitness tracking system of FIG. 1.

With reference now to FIG. 3, an exemplary activity tracking system is shown wherein at least one shoe 12 is selected from a plurality of shoes and paired to a smartwatch 30a and/or a smartphone 30b via the network 50/55. In particular, the user purchases a pair of shoes from a vendor who sales various types of shoes (e.g., running shoes, cross-training shoes, etc.) and various models of each type of shoe). The shoes 12 purchased by the user are defined by a particular color or color combination (e.g., white, white/black, black/gold, orange/black, etc.) Such colors are visible on the exterior of the shoe and typically the predominant color or colors of the shoe (e.g., the predominant color(s) of the midsole 14, upper 16 or outsole 18).

After purchasing the shoes 12, the user downloads and opens the fitness app 31 on his or her personal electronic device(s) (i.e., the smartphone 30b and/or the smartwatch 30a). The fitness app 31 provides instructions to the user to pair the shoes with the personal electronic device. For example, the user may be asked to walk with the shoes in order to wake the processor 27 of the activity monitoring device 20 embedded in the shoes 12. When the processor 27 is awakened, pairing requests or other data is automatically transmitted from the activity monitoring device 20. The pairing request generally includes information identifying the make and model of the shoe 12, and may also include other data, such as total steps taken with the shoe or distance travelled with the shoe.

When a personal monitoring device 30 that includes the fitness app 31 receives a pairing request from the shoe 12, the personal electronic device 30 processes the request and establishes communications with the activity monitoring device 20. A "connected" screen 312 is then presented on the display 34 of the personal electronic device 30. In at least one embodiment the connected screen 312 is a drop down screen that automatically slides down from the top edge of the screen 34 when the shoes 12 are paired to the personal electronic device 30. The connected screen 312 includes an indication that communications between the shoe 12 and the personal electronic device 30 have been established, a pictorial representation 314 of the shoes (e.g., a photograph or sketch of the shoes), as well as additional information 316 about the shoes such as the model of the shoes, total steps, or distance travelled with the shoes. As shown in FIG. 3, the connected screen 312 may be configured differently and present different information depending on what type of personal electronic device 30 is paired to the shoes 12. For example, if the personal electronic device 30 is the smart watch 30a, a simplified screen with less information may be shown (e.g., additional information 316 may not be shown). However, if the personal electronic device 30 is the smartphone 30b, additional information (e.g., information 316) may be included on the connected screen 312.

In at least one embodiment the color scheme of the connected screen 312, and particularly the background portion of the connected screen 312 shown on the personal electronic device 30, is the same color scheme as the shoes 12. For example, if the upper 16 of the shoes 12 are mostly (or at least in large part) a shade of orange, the background of the connected screen 312 is the same shade of orange as the upper 16 of the shoes 12. As another example, if the shoes 12 are mostly (or at least in large part, such as 10-50%) comprised of a color scheme that includes shades of blue and gray, the background of the connected screen 312 is the same shade of blue and gray. Furthermore, as noted above, the connected screen 312 may also include a pictorial representation 314 of the shoes, which shows the shoe 12 with the same colors and design as the actual shoe connected to the personal electronic device 30. Because the connected screen 312 not only includes a pictorial representation of the shoe 12, but also includes a background with the same color scheme as the shoes, the user is able to quickly and easily identify that a proper connection has been established between the shoes he/she is wearing and the personal electronic device. On the other hand, if a connected screen with colors that are different from those of the shoe the user wishes to connect are shown, the user may be alerted that the wrong shoes are paired to his or her personal electronic device, and the user may terminate communications and attempt to re-pair the shoes 12 to the personal electronic device.

Training Plans

Figure 4:
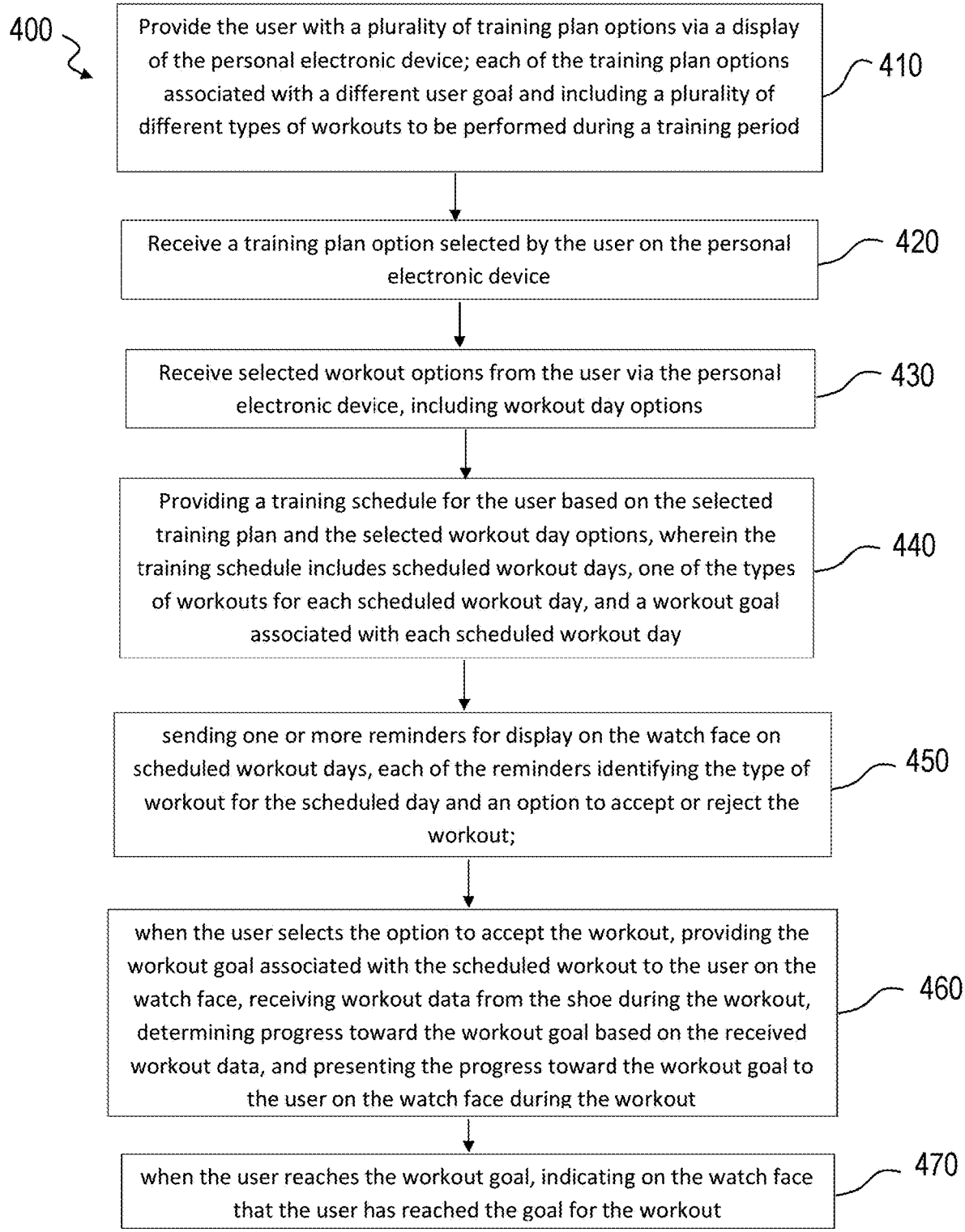
FIG. 4 is a flowchart of a method of providing workout training for a user of an activity tracking system.

As described above, the fitness tracking system 10 includes a number of different components, such as shoes 12, one or more activity monitoring devices 20, and one or more personal electronic devices 30. In at least one embodiment, the fitness app 31 provided on the personal electronic device 30 provides the user with the ability to select and implement one of a number of different training plans via the display of the personal electronic device 30. FIG. 4 shows a flowchart of an exemplary method 400 for providing workout training for a user of a fitness tracking system. The method includes each of acts 410-470, which are all explained in further detail below in association with additional FIGS. 5-14.

The method 400 begins with act 410 wherein the fitness app 31 provides the user with a plurality of training plan options via a display of the smartphone 30b or other personal electronic device. The plurality of training plan options may be presented to the user in any of various forms, such as a menu or list of training plans for review by the user. In at least one embodiment, the training plans options are presented in a menu-like form and organized by category. Example categories for the training plan options include race plans (e.g., 5K, 10K, half marathon, marathon, etc.), general fitness and power plans (e.g., "get in shape," "get strong," etc.), weight-loss plans (i.e., a plan that helps the user loose a desired amount of weight by integrating running with a diet plan), learning-to-run plans (i.e., a plan that teaches a new runner proper pace, stride length, cadence based on the demographics of the individual runner), and custom plans (i.e., custom distance plans, combinations of other plans to meet desired goals of the user). Each training plan option presented to the user includes additional descriptive information in order to help the user decide if a particular training plan is right for him or her.

Figure 5:
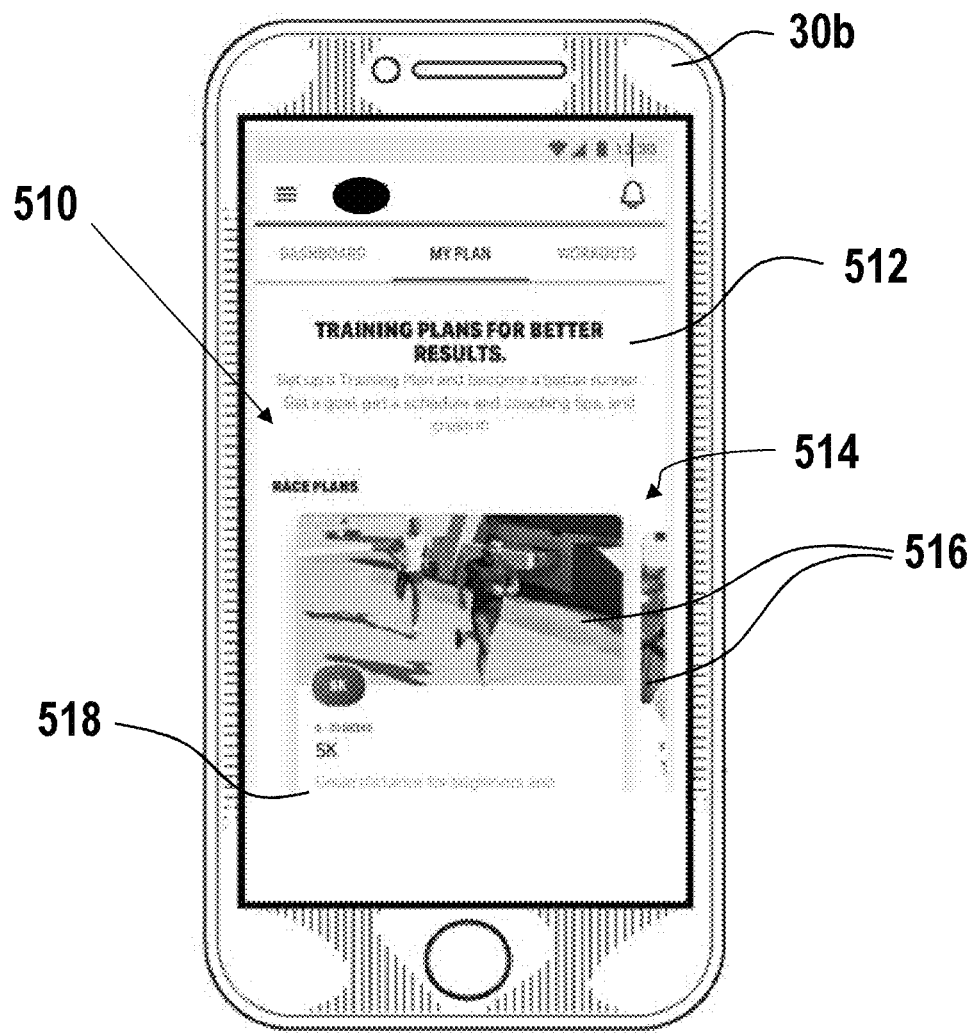
FIG. 5 is a front view of the smartphone of FIG. 3 showing an exemplary fitness app for an activity tracking system, the fitness app providing a display screen that enables a user to select a training plan.

With reference now to FIG. 5, an exemplary options screen 510 of the fitness app 31 is shown on the display of the user's smartphone 30b. The exemplary options screen 510 includes a header 512 that invites the user to set up a training plan in order to achieve better fitness results. A menu 514 of training plan options is provided under the header 512. The menu 514 includes several training plan categories (e.g., race plans, general fitness/power plans, weight-loss plans, etc.) with one or more different plans 516 listed under each category. The user may swipe vertically to view different categories of race plans offered on the menu 514 and then swipe horizontally to view different plans 516 within a selected category. For example, if the user swipes vertically and reaches the "Race Plans" category, the user may then swipe horizontally and find the following race plans: "Complete a 5K," "Finish a 10K," "Half Marathon Training," "Marathon Coaching," and "Custom Distance." Each race plan includes additional information 518 to help the user decide if that particular plan is appropriate for the user. For example, under the "Complete a 5K" plan, the following description is provided: "For beginners or those working on speed, we'll get you to the finish line." If the user then selects that plan option 516 additional options (not shown) to tailor the plan to the individual are provided. For example, after selecting the "Complete a 5K" plan option, the user is presented with the following two options on the options screen 510 or a subsequent screen: "Train for Distance (this is your first time running this distance)" and "Train for Pace (you're comfortable running this distance and want to improve your finish time)."

After choosing one of the training plan options 516 from the options screen 510, the user may then presented with an additional screen (not shown) and invited to input additional requested information via the fitness tracking app 31 in order to determine a specific training plan that is best for the user. For example, the user may be asked how far he or she typically runs in a week or on a per workout basis, and at what pace. After inputting this information, the user may then be invited to select a specific plan that calls for some number of workouts per week that may be best suited for the user. For example, an easier training plan may call for three or four runs per week, while a harder plan may call for four or five runs per week. Thus, a runner who wants to only train three days per week may choose the easier plan, while a runner willing to run five days a week may choose the harder plan.

With reference again to FIG. 4, after the user selects one of the training plans presented in block 410, the method continues at block 420, and the selected training plan is received by the system 100. In response to receipt of a selected training plan, the system 100 generates a series of additional screens requesting workout options from the user during the duration of the training plan. These workout options allow the system to customize the selected training plan for the specific user. For example, with reference now to FIG. 6, after the user selected the "5K" race plan, a scheduling screen 610 is presented to the user. The scheduling screen 610 gives the user a start date 612 and an end date 614 that covers the duration of the training plan (e.g., a start date of today, and an end date 12 weeks later, if the recommended duration of the training plan is 12 weeks). However, if the user selects either of these dates 612, 614, the user is provided with the ability to change the start and end dates. As noted in the text above the start and end dates

612, 614, the selected training plan must have some minimum duration (e.g., 12 weeks), but the user may also extend the duration of the training plan to longer than the minimum duration if desired (e.g., from 12 to 20 weeks).

With continued reference to FIG. 6, below the start and end dates 612, 614, is a weekly run scheduler 616 where the user is asked to input the days of the week on which they would like to run. The weekly run scheduler 616 includes a block of workout day options 618, which a list of the seven days of the week (e.g., Sun-Sat, in abbreviated form) and an associated option for each day. The user then selects the days on which they would like to run, and these selection become scheduled workout days for the duration of the training plan (although some training plans may include one or more rest days in a given week during the plan wherein the user does not workout even if the user selected that day on the workout day options). The run scheduler 616 provides a recommendation for the number of days the user should run each week under the selected training plan, and asks the user to select some number of days that is close to that number. For example, if the run scheduler 616 recommends that the user runs five days a week under the selected training plan, the user is asked to select 4, 5 or 6 days of the week in which the user intends to run. In the exemplary embodiment of FIG. 6, the list 618 shows that the user selected four days of the week (i.e., Sunday, Monday, Wednesday and Friday) in which to run, and the associated circles under those days are filled-in on the list 618 to indicate that those days were selected by the user.

In addition to the list 618, the run scheduler 616 may also include a long run option 620 that asks the user to select at least one day of the week in which to perform a "long run." Long runs are typically associated with race plans where the user is attempting to achieve a goal of running a particular distance at a desired pace, but may also be associated with any of various other plans. In the exemplary embodiment of FIG. 6, the user has selected "Sunday" as the day on which they would like to perform a long run.

Figure 6:
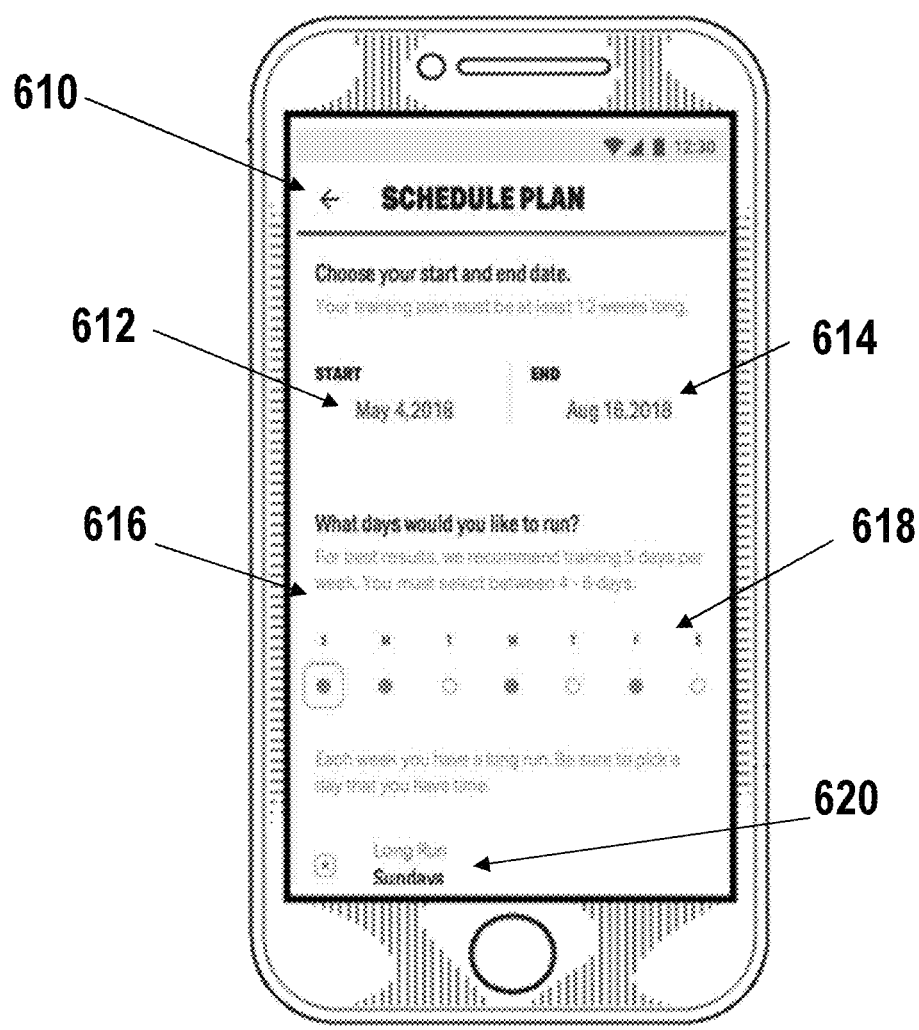
FIG. 6 is a front view of the smartphone of FIG. 3 showing an exemplary fitness app providing a display screen that enables a user to select workout days and other options for a selected training plan.

With reference again to FIG. 4, as various workout options are selected by the user (such as the above-discussed options associated with scheduling screen 610 of FIG. 6), those workout options are received by the system, as noted in block 430. Then, as noted in block 440, the system 100 generates a training schedule for the user based on the training plan selected by the user and the various workout options received from the user, including the workout day options 618 and the long run option 620. The training schedule includes a calendar that shows scheduled workout days. The training schedule also includes a specific type of workout for each of the scheduled workout days. The training schedule may also include a goal for each scheduled workout.

Figure 7:
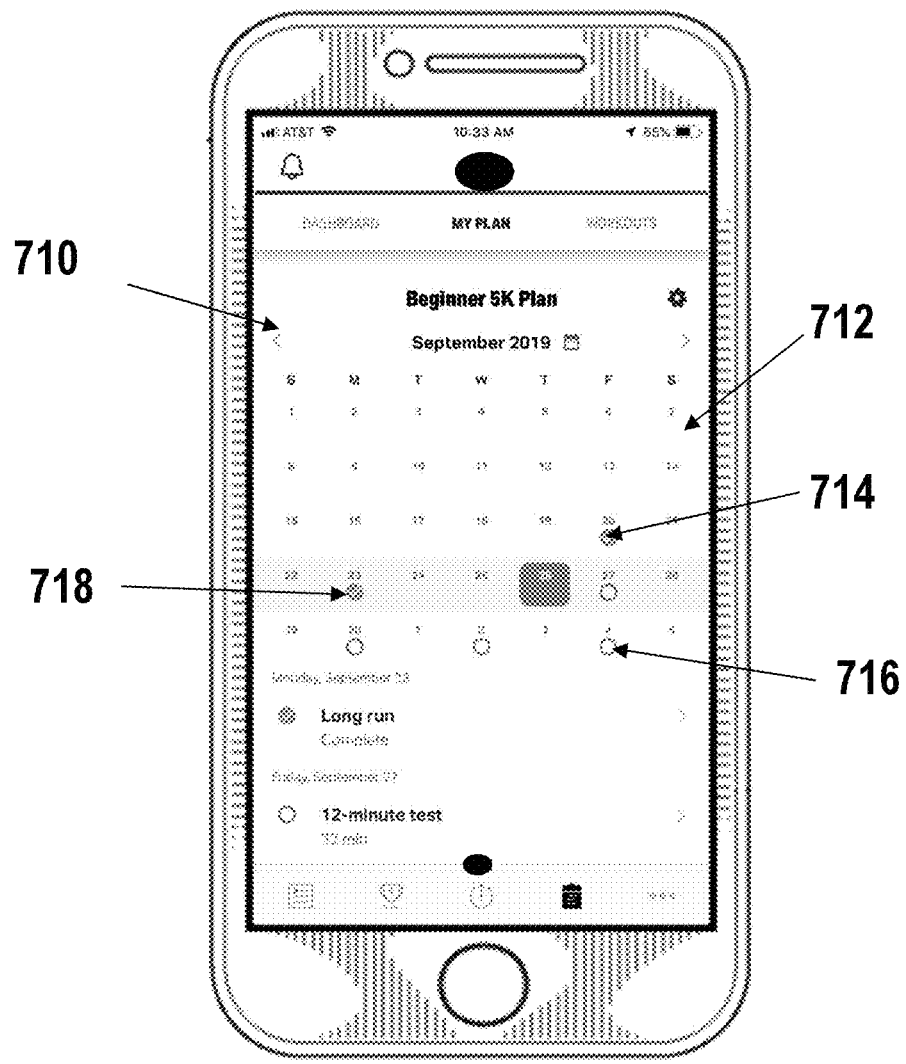
FIG. 7 is a front view of the smartphone of FIG. 3 showing an exemplary fitness app providing a display screen with training details for a scheduled workout.

With reference now to FIG. 7, a training schedule screen 710 is shown. The training schedule screen 710 includes a calendar 712 where the user may scroll from month-to-month within the calendar. The calendar 712 includes an icon 714 or other indication of each scheduled workout day during the training plan. In the embodiment of FIG. 7, the indication is a circle under each workout day. If the workout day is in the future, the circle is blank and unfilled (e.g., see circle 716). If the workout day is in the past, and the user completed a workout on that day, the circle is filled-in with a color and a check mark is provided inside of the circle (e.g., see circle 718). If the user did not complete a workout on a scheduled workout day, the circle is removed from the calendar 712 (e.g., a circle was removed from association with September 25).

In addition to showing whether a workout is complete or incomplete, the training schedule screen 710 also indicates a type of workout for each scheduled workout day. For example, as shown on the lower portion of the training schedule screen 710 of FIG. 7, a long run was completed on September 23. Similarly, a 12-minute test is scheduled for September 27. If the user wishes to view details for any workout day, the user simply clicks on the icon 714 associated with the workout. If the workout was previously completed, a screen with workout parameters such as time, distance, pace, cadence, heart rate, etc. is presented to the user. If a goal was associated with the workout, this screen may also indicate whether the goal was met. If the workout has yet-to-be-completed, a screen with information about the workout planned for that day is presented to the user.

Figure 8:
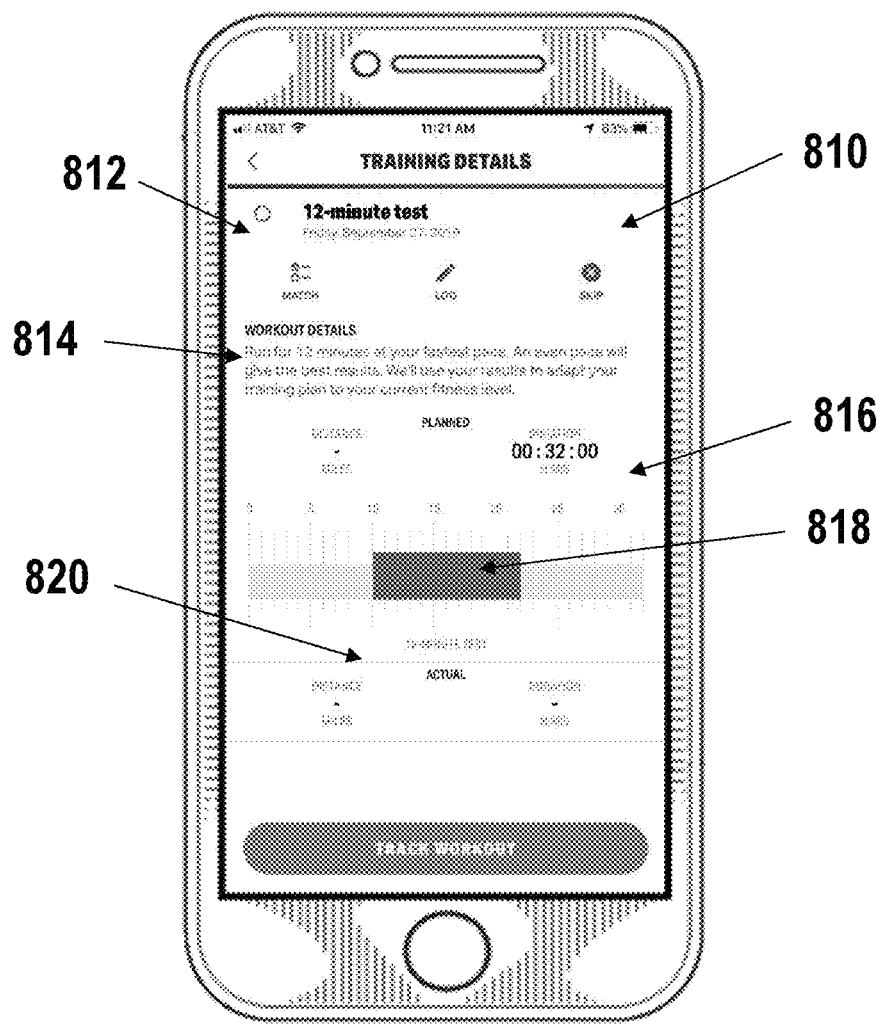
FIG. 8 is a front view of the watch of FIG. 3 with an exemplary watch face showing a reminder for a scheduled workout provided on the watch face.

FIG. 8 shows an exemplary training details screen 810 shown to the user following selection of a yet-to-be-completed workout. As shown in FIG. 8, the training details screen includes a header 812 showing a title or type of workout to be completed, a details section 814 explaining the workout in detail, a graphics section 816 illustrating what the user will be asked to do during workout, and a workout parameters section 820 which is not completed until the user actually finishes the workout. In the example of FIG. 8, the header 812 indicates that the workout to be completed on September 27 is a "12-minute test." The details section 814 explains that the user will run for 12 minutes at his or her fastest pace in the middle of the workout. The graphics section 816 includes a timeline showing that the workout is a 32 minute run that begins and ends with ten minutes at an even pace. A highlighted block 818 in the middle of the timeline illustrates when the 12-minute test at the user's fastest pace will occur.

Figure 9:
FIG. 9 is a front view of the watch of FIG. 3 with an exemplary watch face showing an option to begin a workout.

Returning again to FIG. 4, after the training schedule is generated and provided to the user, as noted in block 440, the method continues by implementing the training program. Implementation of the training program includes sending various reminders to the user on a watch face, as indicated in block 450. Each of the reminders identifies the type of workout for the scheduled day (e.g., a "long run," "12-minute test," etc.), along with an option to accept or reject the workout. FIG. 9 shows an exemplary watch 30a including a workout reminder screen 910 displayed on the watch face 34a. The workout reminder screen 910 includes an "accept" option 912, a "reject" option 914, a workout description section 916, and a workout details section 918. The workout reminder screen 910 may be scheduled by the user for presentation at one or multiple times during the day. For example, the workout reminder screen 910 may be presented to the user in the morning along with a wake-up alarm. As another example, the workout reminder screen 910 may be scheduled as an alarm itself at or before the typical time the user intends to workout (e.g., at 11 am, noon, 5 pm, etc.) Before deciding to accept or reject the workout, the user may review the workout description section 916, which shows the user the title of the workout, the length of the run (if any), and estimated time for the workout. If the user would like additional information concerning the scheduled workout, the user may review the workout details section 918 by scrolling the workout details section 918 upward into the middle of the watch face 34a. The workout details section 918 provides additional information concerning the workout, including the rationale for the type of workout and how the workout fits in the user's training plan. If the user selects the accept option 912, the workout remains in the schedule for the day. On the other hand, if the user selects the reject option 914, the workout is removed from the schedule for the day.

If the user decides to reject the workout from the workout reminder screen 910 (i.e., by selecting the "reject" option 914), the user may be presented with an option to amend the training schedule. For example, if the user decides to reject a Monday workout, the user may be asked if he or she now wishes to a different workout on Monday or perform the same workout on Tuesday. If the user consistently makes changes to the workout schedule by rejecting workouts, the system may determine that the current training plan is not appropriate for the user. For example, if a user rejects three workouts in a row, or rejects three Monday workouts in a row, the system may determine that the user may have given up on the training plan or would like to amend the training plan. In this case, the system may present the user with a screen asking the user if they would like to cancel or amend the training plan in some manner. The system may further be configured to provide recommended amendments to the training plan based on the user's behavior. For example, the system may recommend that the user change the designated long run workout day to a different day based on repeated changes to the long run workout day. As another example, the system may recommend that the user enroll in a different training plan (e.g., a 5K instead of a 10K) based on the number of days of the week and amount of time that the user is actually performing workouts.

With reference again to FIG. 4, if the user does decide to accept the workout, the method moves on to block 460. As noted in block 460, if the user accepts the workout the user is provided with a goal for the workout on the watch face. The user then begins the workout, and workout data from the activity monitoring device 20 (e.g., the monitoring device included on the user's shoe 12) is received by the watch 30*a*. Then, during the workout, progress toward the workout goal is presented to the user via the watch face 34*a*. As noted in block 470, when the user reaches the workout goal, an indicia is provided on the watch fact informing the user that they have reached the goal for the workout. An exemplary watch face providing such information to the user during a workout is provided below in association with FIGS. 10-14.

Dynamic Coaching on GUI During Workout

Figure 10:
FIG. 10 is a front view of the watch of FIG. 3 with an exemplary watch face showing an arced bar illustrating progress toward a duration goal for a workout.

With particular reference now to FIG. 10, an exemplary start workout screen 1010 is shown. The start workout screen 1010 may be presented to the user immediately after has accepted a workout from the workout reminder screen 910, or may be presented to the user when the user opens the fitness app 31 when a workout is scheduled for that day. The start workout screen includes a workout description section 912, a goal option 914, and a start workout option 916. The workout description section 912 provides a brief description of the planned workout to be performed (e.g., "long run"). The goal option 914 allows the user to view another screen and see the current goal for the workout set by the system (e.g., run for 30 minutes) and/or add additional goals (e.g., run 5 miles). When the start workout option 916 is selected, the system begins tracking the workout.

Figure 11:
FIG. 11 is a front view of the watch of FIG. 3 with an exemplary watch face showing an arced bar illustrating progress toward a distance goal for a workout.
Figure 12:
FIG. 12 is a front view of the watch of FIG. 3 with an exemplary watch face showing an arced bar illustrating a pace during the workout.

FIGS. 11-12 shows a two exemplary workout parameters screens 1110, 1210, 1310, which are available to the user during the workout. These screens provide the user with data about the current workout and thereby offer coaching to the user that will allow the user to meet his or her workout goal. The user may move between these screens by swiping horizontally across the watch face to view the next screen. FIG. 11 shows a workout duration screen 1110 which includes the total time elapsed for the workout, time remaining to reach the goal, and a goal progress arc 1112. The goal progress arc 1112 is an arced bar that spans an angle that is directly associated with the user's goal. One end 1114 of the arc represents the start of progress toward the goal (e.g., zero). An opposite end 1116 of the arc represents completion of the goal (e.g., thirty minutes). As the user progresses toward the goal, an associated amount of the arc is filled-in (e.g., with a color, illumination, or other representation). The portion of the arc 1112 that is not filled-in (e.g., dim, blank or colorless) represents how much remains for the user to reach his or her goal. In the example of FIG. 11, the user has completed 23:45 toward the 30:00 goal and has 6:15 remaining. Accordingly, an associated portion of the goal progress arc 1112 is filled-in (i.e., 23:45/30:00), and an associated portion of the goal progress arc is not filled-in (i.e., 6:15/30:00).

FIG. 12 shows a workout distance screen 1210 which includes the total distance traversed for the workout, total duration of the workout, and a goal progress arc 1212. The goal progress arc 1212 is an arced bar that is similar to the arc 1112 of FIG. 11, and spans an angle that is directly associated with the user's goal. As the user progresses toward the goal, an associated amount of the arc is filled-in. In the example of FIG. 12, the user has completed 2.58 miles of a 5.0 mile goal Accordingly, an associated portion of the goal progress arc 1212 is filled-in (i.e., 2.58/5.0), and an associated portion of the goal progress arc is not filled-in (i.e., 2.42/5.0).

Figure 13:
FIG. 13 is a front view of the watch of FIG. 3 with an exemplary watch face showing a completely filled arced bar when a duration goal for the workout is met.

When the user meets the workout goal during a workout, the goal progress arc is fully filled-in. For example, in the embodiment of FIG. 13, the goal progress arc 1312 provided on the workout distance screen 1310 shows that the user had a goal to run 8 kilometers. During the run, the goal progress arc 1312 is progressively filled in with a green color until it is completely filled in upon the user reaching the 8 kilometer mark. At the moment the goal progress arc 1312 is completely filled in, the watch provides an additional indication of goal attainment to the user. This additional indication of goal attainment may be provided in any of various forms, such as audio, visual or haptic feedback to the user via the watch. In at least one embodiment the goal progress bar 1312 displayed on the watch face is made to shimmer, shine or is otherwise emphasized to show the user that he or she has reached to workout goal. As shown in FIG. 13, an additional indicator 1320 in the form of a check mark with the word "Goal!" may also be provided on the watch face in order to indicate to the user that he or she reached the workout goal.

In at least one embodiment, the activity data collected from a workout is used to modify future goals for the user. For example, consider a user presented with a goal to complete a long run of six miles in under an hour. If the user is only able to run five miles in the allotted hour, future goals for long runs may be modified. For example, the long run scheduled for the next week may be modified from six miles in one hour to five-and-a-half miles. As another example, if the user actually ran seven miles in an hour where the goal was six miles, the goal for the next long run may be seven and a quarter miles. The system is configured to make similar modifications to future workouts based on the results of other planned workouts within the training period. For segmented runs (e.g., the 12-minute test), goals for future workouts may depend at least in part on the performance of the user during particular segments of the run. For example, if a user runs 1.5 miles in a 12-minute test, and this pace surpassed the system's expected pace of the user, future workout goals may be modified accordingly. Therefore, it will be recognized that, in addition to providing workout data to the user that includes performance metrics and goal attainment, the system is further capable of dynamically modifying scheduled workouts within a training plan based on user performance during individual workouts.

Figure 14:
FIG. 14 is a front view of the watch of FIG. 3 with an exemplary watch face showing a cadence of the user within a cadence target range.

In addition to providing a goal progress arc or other indicator that shows the user progress toward his or her workout goal, the fitness tracking system 100 includes additional features designed to assist and/or coach the user in reaching a workout goal or otherwise achieving a productive workout. For example, FIG. 14 shows a workout pace screen 1410 that assists the user in determining whether his or her current pace will allow the user to reach a workout goal of a certain distance within a given period of time. The user may review this screen by swiping horizontally across the watch face from one of the related screens showing a workout progress arc (e.g., screens 11 and 12). The workout pace screen 1410 shows the user's instantaneous/current pace (i.e., 8.32 min/mi), and the average pace for the entire workout (i.e., 9.20). The workout pace screen 1410 also includes a multi-section goal coaching arc 1412 provided along the upper portion of the screen. The goal coaching arc 1412 is an arced bar that is split into multiple sections, 1414, 1416 and 1418, with a break separating each section from an adjacent section (i.e., each section includes two clearly defined ends such that each section is separate from an adjacent section).

In the embodiment of FIG. 14, the first section 1414 of the goal coaching arc 1412 is a center section that illustrates a range for a target pace that will allow the user to meet a particular goal for the workout (e.g., run a 5K in 25 minutes). The first section 1414 includes a recommended maximum pace for the user on a left side of the section 1414 (i.e., see "8:55" in proximity of the left side break in the arc 1412 in the example of FIG. 14), and a recommended minimum pace for the user on a right side of the section 1414 (i.e., see "8:05" in proximity of the right side break in the arc 1412 in the example of FIG. 14). The recommended minimum and maximum pace is based on a number of different parameters including not only the user's goal for the workout, but also the user's historical workout parameters (e.g., average pace for runs of similar length over some recent period such as a past month) and personal demographic information (e.g., age, sex, weight, max heart rate, etc.). The second section 1416 is positioned to the left of the center section 1414 and represents paces that fall below the target pace (i.e., slower paces that will not allow the user to meet the goal). The third section 1418 is positioned to the right of the center section and represents paces that are well above the target pace (i.e., faster paces that will theoretically allow the user to meet the goal, but are not recommended for this user for various reasons, such as a pace that is too fast and will likely result in user fatigue based on the workout history and personal demographics of the user). The user's current pace is not only shown in the center of the screen, but is represented on the goal coaching arc 1412 by the indicator 1420 (which is an arrowhead in the embodiment of FIG. 14). The section of the goal coaching arc 1412 that includes the indicator 1420 is also highlighted in some manner, such as enlarged relative to the other sections and/or filled with a color. This provides additional assistance to the user in quickly identify whether his or her current pace is an acceptable pace toward meeting the workout goal. In the example of FIG. 14, the user's current pace of 8:32 is near the middle of the target pace, so the indicator 1420 points to the middle of the first section 1414, and this section 1414 is filled with a green color and slightly enlarged relative to the other sections 1416 and 1418. When the user's current pace is above or below the target pace range, the associated section 1416 or 1418 is enlarged and filled with a different color, such as a red color, to indicate that the user should change the current pace of the workout.

As noted above, the goal coaching arc of FIG. 14 is particularly advantageous to the user during a workout because it allows the user to quickly view his or her current pace and immediately discern whether the current pace is within a target range that will allow the user to meet the workout goal (or is outside of the target range such that he or she is unlikely to meet the workout goal). By periodically checking the goal coaching bar 1412 during the workout (i.e., by glancing at the watch face), the user receives direction on whether he or she should speed-up or slow-down in order to meet the workout goal. If the user sees that the indicator 1420 is within the first section 1414 associated target pace range, the user knows that continuing on this pace will allow the user to meet the workout goal. If the user sees that the indicator 1420 is in the second section 1416 below the target pace range, the user knows to speed up the pace. If the user sees that the indicator 1420 is in the third section 1418 above the range for the target pace, the user knows to slow down the pace.

With continued reference to FIG. 14, in at least some embodiments, the goal coaching arc 1412 is dynamic such that the target range associated with the center section 1414 changes throughout the workout. In this embodiment, the target pace range (i.e., at the center section 1414) may change throughout the workout in order to show the user the pace needed to reach his or her workout goal. Therefore, the target range for the user's running pace may be one range at beginning of a workout and the target range may progressively widen or narrow depending on whether the user begins the run at a faster or slower pace necessary to achieve the workout goal. For example, consider a user with a goal to run three miles in 24 minutes (i.e., an average pace of 8 minutes per mile). If the user decides to start the run slower and finish faster, the target range for the user will progressively narrow during the workout (e.g., an original target pace between 7:45 and 8:15 minutes/mile may change to a target pace between 8:15 and 8:30 minutes/mile later in the workout). On the other hand, if the user decides to start the run more quickly and slow down toward the end, the target range will progressively widen during the workout (e.g., an original target pace between 7:45 and 8:15 minutes/mile may change to a target pace between 7:45 and 8:00 minutes/mile later in the workout). Accordingly, it will be recognized that in at least some embodiments goal coaching arc 1412 is dynamic and associated with a target range that will assist the user in meeting a particular workout goal related to a pace (i.e., a specific distance within a given period of time). The goal coaching arc 1412 includes a dynamically adjustable target range with an upper value and a lower value that change based on prior pace values recorded during the workout.

In addition to the providing coaching on the watch face that allows the user to meet a specific distance goal within a given time (i.e., a pace goal), the system may also provide coaching that allows the user to meet other workout goals, such as proper running form. For example, FIGS. 15-18 show a watch face with a cadence screen 1510 including goal coaching arc 1512 that allows a user to achieve a proper cadence that is related to the user's current pace. As shown in FIG. 15, the goal coaching arc 1512 is an arced bar that is split into multiple sections, 1514, 1516 and 1518, with a break separating each section from an adjacent section (i.e., each section includes two clearly defined ends such that each section is separate from an adjacent section).

In the embodiment of FIGS. 15-18, the first section 1514 of the goal coaching arc 1512 is a center section that illustrates a range for a target cadence (in steps per minute) that will assist the user in achieving a proper running form based on their current pace (e.g., a pace of 8 minutes 32 seconds per mile). The first section 1514 includes a recommended minimum cadence on a left side of the section 1514 (i.e., see "154" at the left side break in the arc 1512 in the example of FIG. 15), and a recommended maximum cadence for the user on a right side of the section 1514 (i.e., see "170" at the right side break in the arc 1512 in the example of FIG. 15). The recommended minimum and maximum cadence is based on a number of different parameters including the user's historical workout parameters (e.g., average pace for runs of similar length over some recent period such as a past month), personal demographic information (e.g., age, height, sex, weight, etc.), and objective research data showing best cadences for running (e.g., based on achieving maximum speed, maximum distance, injury prevention over time, etc.).

As shown in FIG. 16, the second section 1516 of the goal coaching arc 1512 is positioned to the left of the center section 1514 and represents a cadence that falls below the target cadence for the user (i.e., a cadence that is too slow based on the user's current pace). As shown in FIG. 17, the third section 1518 of the goal coaching arc 1512 is positioned to the right of the center section 1514 and represents a cadence that is above the target cadence for the user (i.e., a cadence that is too fast based on the user's current pace). The user's current cadence and pace are both displayed under the goal coaching arc 1512. In addition to the actual value for the user's cadence being positioned at the center of the screen, the value is also represented on the goal coaching arc 1512 by the indicator 1520 (which is an arrowhead in the embodiment of FIGS. 15-17). The section of the goal coaching arc 1512 that includes the indicator 1520 is also highlighted in some manner, such as enlarged relative to the other sections and/or filled with a color. This provides additional assistance to the user in quickly identify whether his or her current cadence is an acceptable cadence in relation to the user's current pace. In the example of FIG. 15, the user's current cadence of 165 steps/minute is near the middle-upper of the target cadence, so the indicator 1520 points to the middle-right of the first section 1514, and this section 1514 is filled with a green color and slightly enlarged relative to the other sections 1516 and 1518. As shown in FIG. 16, the user's current cadence has dropped to 148 steps/minute, which is below the target cadence range, so the indicator points to the second section 1516, and this section is filled with a red color and slightly enlarged relative to the other sections 1514 and 1518. Similarly, as shown in FIG. 17, the user's current cadence has increased to 178 steps/minute, which is above the target cadence range, so the indicator points to the third section 1518, and this section is filled with a red color and slightly enlarged relative to the other sections 1514 and 1516. When the user's current pace is above or below the target cadence range, indicator and the associated red color on the goal coaching arc 1512 quickly provide the user with an indication that he or she should change the current cadence of the workout.

Figure 18:
FIG. 18 is a front view of the smartphone of FIG. 3 showing an exemplary fitness app providing a display screen showing scheduled and completed workouts for a selected training plan.

The goal coaching arc 1512 shown in FIGS. 15-17 is particularly advantageous to the user during a workout because it allows the user to quickly view his or her current cadence and immediately discern whether cadence is within a target range for the user's current pace. By periodically checking the goal coaching arc 1512 during the workout (i.e., by glancing at the watch face), the user receives direction on whether he or she should change his or her cadence in order to adopt a healthier or more efficient running form. If the user sees that the indicator 1520 is within the first section 1514 associated with the target cadence, the user knows that his or her current cadence is proper. If the user sees that the indicator 1520 is in the second section 1516 below the target cadence, the user knows to increase his or her cadence. If the user sees that the indicator 1420 is in the third section 1518 above the target cadence range, the user knows to decrease his or her cadence. As noted previously, the target cadence range displayed in association with the first section 1514 is dynamically adjustable in relation to the user's current pace for the workout. FIG. 18 shows the watch of FIGS. 15-17 with the user's pace changed to a slower pace (i.e. in FIGS. 15-17 the pace is 8:32 min/mile, and in FIG. 18 the pace is 9:15 min/mile). Accordingly, the first section 1514 of the goal coaching arc 1512 has changed such that a lower end of the target range is 140 (as shown in association with the left side of the first section 1514) and an upper end of the target range is 155 (as shown in association with the right side of the first section 1514). In this example, the user's cadence is 148 steps/min. In FIG. 16, this same cadence of 148 steps/min resulted in the indicator 1520 pointing to the second section 1516 of the goal coaching arc 1512, below the target cadence range for the pace of 8:32 min/mile. However, in FIG. 18, a cadence of 148 steps/minute is determined to be proper for the user's pace of 9:15 min/mile, so the indicator 1520 points to the second section 1514 of the goal coaching arc, indicating that the current cadence is proper in relation to the current pace. Accordingly, it will be recognized that the goal coaching arc 1512 is dynamic and configured to assist the user in achieving a proper running form wherein the user's current cadence is proper for his or her current pace. The goal coaching arc 1512 includes a target range that is dynamically adjusted during the workout based on current pace data.

Exemplary Activity Monitoring Devices

With reference again to FIGS. 1-2, additional detail concerning the various components of an exemplary fitness tracking system 10 capable of performing the above-described methods and offering the associated features is now provided.

As noted previously, the fitness data accumulated during an activity or workout may be collected automatically by a sensor of the activity monitoring device 20. In at least one embodiment, the activity monitoring device 20 is integrated into or otherwise coupled to a running shoe 12 and is configured to measure fitness data relating to user's running or walking. Particularly, the activity monitoring device 20 is configured to measure one or more of steps, distance, speed, stride length, stride cadence, pronation/supination angles, ground contact time, foot strike forces/directions, stairs climbed, as well as various other types of activity data or physiological data.

In the exemplary embodiment shown in FIG. 1, the activity monitoring device 20 is provided as a sensor device that is integrated within the running shoe 12 or footwear. In at least one embodiment, the activity monitoring device 20 is non-removably embedded in a mid-sole 14 of the running shoe 12. However, in other embodiments, the activity monitoring device 20a may removably inserted into a portion of the shoe 12 or clipped, attached, or otherwise secured to an external surface of the shoe 12. As used herein, the term "shoe" refers to any type of footwear, such as tennis shoes, running shoes, casual shoes, boots, cleats, sandals, socks, or any other article of footwear worn on a foot. In one embodiment, the activity monitoring device 20 includes a protective outer shell or housing 22 designed to retain and protect various sensors and other electronic components positioned within the housing 22. The housing 22 comprise any number of shapes, configurations, and/or materials, the description herein being merely exemplary. In at least one embodiment, the housing 22 comprises a relatively rigid shell that securely retains the electronic components housed therein.

In at least one embodiment, the electronic display device 30 also serves as an activity monitoring device 20. For example, the smartwatch 30a and/or smartphone 30b may also serve as an electronic monitoring device 20 that the user straps to his or her arm or wrist, or otherwise carries during a workout. It will be recognized that in other embodiments, further activity monitoring devices may be provided in any of various different configurations to be worn on any of various locations on the body of the user, such as via a module that clips on to clothing, is worn on a chest strap, fits in a pocket of the user, and/or is incorporated into a garment other than a shoe. Additional or alternative examples of activity monitoring devices include those sold under the trademarks FITBIT®, GARMIN®, JAWBONE®, POLAR®, SAMSUNG®, and APPLE®.

Figure 2:
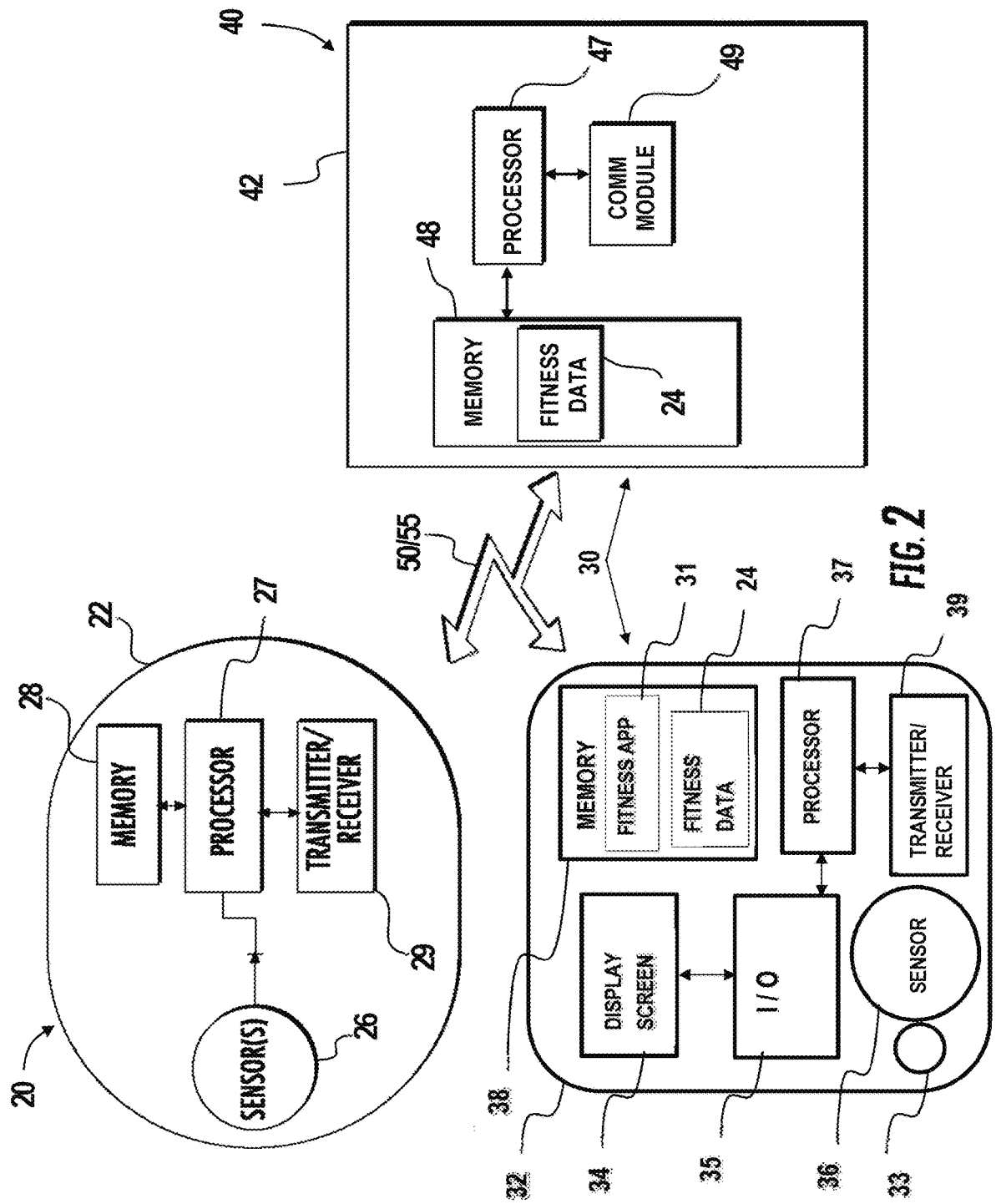
FIG. 2 is a block diagram of exemplary electronic components in the activity monitoring devices, the electronic display device, and the system server of the fitness tracking system of FIG. 1.

With particular reference now to FIG. 2, the activity monitoring device 20 includes electronic circuitry comprising, one or more sensors 26, a processor 27, a memory 28, and a transmitter/receiver 29. The activity monitoring device 20 also include a battery or other power source (not shown) configured to power the various electronic devices within the activity monitoring device 20. In one embodiment, the battery of the activity monitoring device 20 is a long life non-rechargeable battery designed to last longer than the expected life of the shoe 12. In another embodiment, the battery of the activity monitoring device 20 is a rechargeable battery. In this embodiment, the activity monitoring device 20 may be placed in or connected to a battery charger configured for use with the activity monitoring device 20 in order to recharge the battery.

The sensor(s) 26 of the activity monitoring device 20 may comprise any of various devices configured to collect the fitness data, including step data, stride length data, stride cadence data, pronation/supination angle data, ground contact time data, foot strike force/direction data, other motion data, distance traversal data, pace data, GPS data, altitude data, heart rate data, breathing data, environmental/positional data, and/or any of various other types of fitness data that may be relevant to determining activities of the wearer. In at least one embodiment, the sensors 26 of the activity monitoring device 20 include a 3-axis accelerometer configured to detect the motions of the wearer during running or walking, in particular the user's gait or form while running or walking. Of course, it will be recognized by those of ordinary skill in the art that numerous other sensors may be used, depending on the type of activity the activity monitoring device 20 is designed to detect.

With continued reference to FIG. 2, the processor 27 may be any of various microprocessors as will be recognized by those of ordinary skill in the art. The processor 27 is configured to receive data signals from the sensors 26, and other component parts of the activity monitoring device 20 (such as the memory 28), and process such signals. The processor 27 is connected to the memory 28 and the transmitter/receiver 29, and may deliver processed data to one or both of the memory 28 and the transmitter/receiver 29. Additionally, the processor 27 may perform some processing on the received data prior to delivery thereof to the memory 28 or the transmitter/receiver 29. For example, the processor 27 may associate the fitness data with a particular time, day, user (in the instance that the device is configured to collect data relating to more than one user), and/or event.

The memory 28 is configured to store information, including both data and instructions. The data may be retrieved from the processor 27 and generally includes fitness data, but may also include various types of operational data that may be ancillary to the basic operation of the activity monitoring device 20. The instructions which are stored at the memory 28 generally include firmware and/or software for execution by the processor 27, such as a program that controls the settings for the sensors 26, a program that controls the receipt of information via the sensors 26, a program that controls the transmission and reception of data via the transmitter/receiver 29, as well as any of various other programs that may be associated with the activity monitoring device 20. Such instructions may be present on the device 20a, 20b at the time of manufacture or may be downloaded thereto via well-known mechanisms. The memory 28 may be of any type capable of storing information accessible by the processor 27, such as a memory card, ROM, RAM, write-capable, read-only memories, or other computer-readable medium. The data may be stored in the memory 28 in a relational database as a table having a plurality of different fields and records, XML documents, or flat files. The data may also be formatted in any computer-readable format such as, but not limited to, binary values, ASCII or Unicode.

The transmitter/receiver 29 in one embodiment comprises an RF transmitter and receiver configured to transmit and receive communications signals over a network 50/55 using a wireless communications technology, such as Wi-Fi or Bluetooth®, using any of various communications protocols, such as TCP/IP. Such transmitter/receivers are well known and will be recognized by those of ordinary skill in the art. The transmitter/receiver 29 is particularly configured to communicate with the electronic display device 30 when the activity monitoring device 20 is within a given short range of the electronic display device 30, and transmit collected fitness data to the electronic display device 30. In at least some embodiments, the transmitter receiver 29 is further configured to communicate directly with the remote server 40 over a relatively long range via the network 50/55.

Exemplary Personal Electronic Devices

With continued reference to FIGS. 1-2, the electronic display device 30 (which may also be referred to herein as a "display device" or a "personal electronic device") may be provided in any of various forms, such as a smartwatch 30a, or a smartphone 30b. As shown in FIG. 2, the electronic display device 30 generally includes a housing 32, a display screen 34, an input/output interface 35, sensors 36, a processor 37, a memory 38, and a transmitter/receiver 39. Additionally, the electronic display device 30 also includes a battery or other power source (not shown) configured to power the electronic components within the electronic display device 30. In at least one embodiment, the electronic display device 30 is a handheld mobile computing device, such as a smartwatch 30a or a smartphone 30b, but it will be appreciated that the electronic display device 30 may alternatively comprise any number of devices. For example, the electronic display device 30 may be a standalone device, such as a desktop PC, and/or smart television. Alternatively, the electronic display device 30 may be any type of portable or other personal electronic device such as a tablet computer, laptop computer, and/or any of various other mobile computing devices. As will be recognized by those of ordinary skill in the art, the components of the electronic display device 30 may vary depending on the type of display device used. Such alternative display devices may include much (but not necessarily all) of the same functionality and components as the electronic display device 30 shown in FIGS. 1 and 2, as well as additional functionality or components necessary for proper functioning thereof (not shown).

With continued reference to FIGS. 1 and 2, the electronic display device 30 includes various features visible on the housing 32, such as buttons 33, the display screen 34, one or more connection ports (not shown), and/or other input/output hardware and software that operate in conjunction with an I/O interface 35. In the embodiment shown, the buttons 33 comprise tactile buttons, switches, and/or toggles. However, in other embodiments, the buttons 33 may also comprise capacitive or resistive touch sensor. The display screen 34 may vary based on the type of device. For example, in the embodiment shown, the display screen 34 may be a smartphone screen or a watch face. In various embodiments, the display screen 34 may be provided by an LCD or LED screen that provides performance metric information (e.g., time, distance, pace, heart rate, progress toward a goal, or some combination thereof, etc.), notifications, text messages, caller ID, etc. to the user. In some embodiments, the display screen 34 is a touch screen display that allows the user to provide inputs to the I/O interface 35 via virtual buttons or other interfaces on the touch screen. Alternatively, in one embodiment, the display screen 34 may simply be one or more colored lights and/or flashing patterns configured to communicate information to the user (e.g., progress towards a goal or other performance metric).

The I/O interface 35 of the electronic display device 30 includes software and hardware configured to facilitate communications with the one or more activity monitoring devices 20 and/or communications to the user him/herself. The hardware includes a display screen 34 configured to visually display graphics, text, and other data to the user. The hardware may also include a microphone and/or speakers to facilitate audio communications with the user and/or verbal entry of commands to the device 30. In at least one embodiment, the display screen 34 is a touch screen display that allows the user to see data presented on the display screen 34 and input data into the electronic display device 30 via a virtual keyboard or other interface on the touch screen. However, other means for receiving user input, such as a physical keyboard, may also be provided with equal success.

The processor 37 of the electronic display device 30 may be any of various processors as will be recognized by those of ordinary skill in the art. The processor 37 is connected to the I/O interface 36, the memory 38, and the transmitter/receiver 39, and is configured to deliver data to and/or receive data from each of these components. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 38 is configured to store information, including both data and instructions. The data may be, for example, fitness data 24 as discussed above, which may be related to the activities, workouts, health and fitness profile, etc. of the user, along with other operational data that may be ancillary to the basic operation of the electronic display device 30 and any applications retained on the electronic display device 30. The instructions which are stored at the memory 38 generally include firmware, an operating system, and/or other software for execution by the processor 37, such as one or more programs that control the settings for the electronic display device, one or more programs that control the output of the display screen 34 on the electronic display device 30, one or more programs that control various applications on the electronic display device 30, one or more programs that control the transmission and reception of data via the transmitter/receiver 39, as well as any of various other programs that may be associated with the electronic display device 30. In at least one embodiment, the instructions stored in the memory 38 include a client-side activity tracking application, and particularly the fitness app 31, capable of performing the above-described methods and serving as a user interface for the fitness tracking system. Accordingly, the activity tracking application is configured to offer the above-described training plans and form coaching features to the user. The activity tracking application is executed by the processor 37 to process such fitness data and presents the fitness data to the user in a graphical format on the display screen 34. The memory 38 may be of any type of device capable of storing information accessible by the processor, such as a memory card, ROM, RAM, write-capable memories, read-only memories, hard drives, discs, flash memory, or any of various other computer-readable medium serving as data storage devices, as will be recognized by those of ordinary skill in the art.

The transmitter/receiver 39 is, in one embodiment, an RF transmitter and receiver configured to transmit and receive communications signals using a wireless communications technology, such as Wi-Fi or Bluetooth®, using any of various communications protocols, such as TCP/IP. Such transmitter/receivers are well known and will be recognized by those of ordinary skill in the art. The transmitter/receiver 39 is particularly configured to communicate with a transmitter/receiver 29 of the activity monitoring device 20. In at least one embodiment, the transmitter/receiver 39 is configured to allow the electronic display device 30 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

As noted above, in at least some embodiments, the electronic display device 30 also functions as a further activity monitoring device and collects certain fitness data independent of the dedicated activity monitoring device 20 (e.g., in addition to the activity monitoring device of the shoe 12). Particularly, the electronic display device 30 includes sensors 36, such as a 3-axis accelerometer, altimeter, etc. (not shown), configured to record fitness data during an activity or workout. In at least one embodiment, the sensors 36 include a GPS receiver configured to record a global position of the user during an activity or workout.

The electronic display device 30 generally includes a protective outer shell or housing 32 designed to retain and protect the electronic components positioned within the housing 32. The housing 32 may comprise any number of shapes, configurations, and/or materials, the description herein being merely exemplary. In at least one embodiment, the housing 32 includes a relatively rigid portion that securely retains the electronic components, and a more resilient portion which functions as an outer layer to provide shock absorption features in the event the device 30 is dropped, falls, or otherwise withstands an amount of force. In embodiments wherein the electronic display device 30 also functions as a further activity monitoring devices, the housing 32 may serve as a common housing for components of the electronic display device 30 and components of the further activity monitoring device.

In at least one embodiment, the instructions stored in the memory 38 of the electronic display device 30 includes a client-side activity tracking application (which may also be referred to herein as the "workout tracking application"), which is executed by the processor 37 to provide a graphical user interface that enables the user to track, view, and manage his or her fitness data. An exemplary client-side activity tracking application was discussed in detail above. In some embodiments, the memory 28 of the activity monitoring device 20 may also include instructions corresponding to the client-side activity tracking application, and may work in combination with the electronic display device 30 to provide the features of the client-side activity tracking application.

Exemplary System Server

With continued reference to FIGS. 1 and 2, the fitness tracking system 10 further includes a remote system server 40. The system server 40 of FIG. 2 is typically provided in a housing, cabinet or the like 42 that is configured in a typical manner for a server or related computing device. The system server 40 includes a processor 47, memory 48, and a network communications module 49. It is appreciated that the embodiment of the system server 40 shown in FIG. 2 is only one exemplary embodiment of a system server 40. As such, the exemplary embodiment of the system server 40 of FIG. 2 is merely representative of any of various manners or configurations of system servers or other data processing systems that are operative in the manner set forth herein.

The processor 47 is operative, configured and/or adapted to operate the system server 40 including the features, functionality, characteristics and/or the like as described herein. To this end, the processor 47 is operably connected to the memory 48 and the network communications module 49. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 48 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 48 is configured to store instructions including a network-side activity tracking application for execution by the processor 47, as well as a database of fitness data 24 for use by at least the network-side activity tracking application. As discussed in greater detail below, the processor 47 is configured to collect and store fitness data 24 relating to a plurality of workouts of a plurality of users of the fitness tracking system 10.

The network communications module 49 of the system server 40 provides an interface that allows for communication with any of various devices using various means. In particular, the network communications module 49 includes a local area network port that allows for communication with any of various local computers housed in the same or nearby facility. In some embodiments, the network communications module 49 further includes a wide area network port that allows for communications with remote computers over the network 50 (e.g., the Internet). Alternatively, the system server 40 communicates with the network 50 via a modem and/or router of the local area network. In one embodiment, the network communications module is equipped with a Wi-Fi transceiver or other wireless communications device. Accordingly, it will be appreciated that communications with the system server 40 may occur via wired communications or via the wireless communications. Communications may be accomplished using any of various known communications protocols.

The system server 40 may further include a power module (not shown) which is operative, adapted and/or configured to supply appropriate electricity to the system server 40 (i.e., including the various components of the system server 40). The power module may operate on standard 120 volt AC electricity, but may alternatively operate on other AC voltages or include DC power supplied by a battery or batteries.

The system server 40 may be accessed locally by an authorized user (i.e., an administrator or operator). To facilitate local access, the system server 40 may include an interactive user interface (not shown). Via the user interface, an operator may access the instructions, including the network-side activity tracking application, and may collect data from and store data to the memory 48. In at least one embodiment, the user interface may suitably include an LCD touch screen or the like, a mouse or other pointing device, a keyboard or other keypad, speakers, and a microphone, as will be recognized by those of ordinary skill in the art. Accordingly, the user interface is configured to provide an administrator or other authorized user with access to the memory 48 and allow the authorized user to amend, manipulate and display information contained within the memory.

Exemplary Fitness Application

The fitness application 31 (which may also be referred to herein as an "activity tracking application") may include a client-side application stored in the memory 38 of the electronic display device 30 and a network-side (i.e., back-end) application stored in the memory 48 of the remote server 40. The activity tracking application includes instructions for enabling a user to track a plurality of performance metrics during an activity or workout. Particularly, the activity tracking application includes instructions for collecting and processing fitness data during an activity or workout to provide various training plans, performance metrics, and coaching to the user, including those features described above in association with FIGS. 3-18. The term "performance metric" as used herein refers to any standard of measurement relevant to an assessment of the performance, fitness, and health of the user during an activity or workout, or series of activities or workouts. In some cases, the raw measured fitness data is processed substantially to provide a performance metric, but in other cases, measured fitness data may simply be organized into a more presentable form to provide the performance metric. Performance metrics can be generally be considered a further type of fitness data, as defined above. Some examples of performance metrics include heart rate sensor data expressed as beats per minute during an activity or workout, acceleration data expressed a total number of steps during an activity or workout, GPS data expressed as a total distance traversed during an activity or workout, GPS data expressed as positions over time and/or a route/path of the user during an activity or workout, GPS data expressed as an speed/pace over time or average speed/pace during an activity or workout, GPS data or altimeter data expressed as an elevation over time during an activity or workout, fitness data expressed as an estimated number of calories burned, time data expressed a total amount of time spent during an activity or workout, and fitness data express as a total number of workouts or number of workouts during a particular time period (e.g., workouts per week). Further exemplary performance metrics may include any parameter of fitness data expressed as an average over a particular duration of time (e.g. the duration of the workout), as a data plot over the particular duration of time, as a maximum or minimum over the particular duration of time, as a value for some point in time of particular interest, or as a percentage of a user's health or fitness goal or other standard.

FIGS. 5-18 show exemplary embodiments of screens displayed on the electronic display device that enable the user to implement training plans, track a plurality of performance metrics during an activity or workout, and receive coaching during the workout. The processor 37 executes instructions of the fitness application 31 stored in the memory 38 to display various screens of the activity tracking system on the display screen 34.

In various embodiments, a permanent copy of the programming instructions for individual ones of the aforementioned applications (e.g., the client-side activity tracking application and the network-side activity tracking application) may be placed into permanent storage devices (such as e.g., memory 28, memory 38a, 38b, and/or memory 48) during manufacture thereof, or in the field, through e.g., a distribution medium such as a compact disc (CD), or through the transmitter/receiver 29 and/or the transmitter/receiver 39 (e.g., from the system server 40). That is, one or more distribution media having an implementation of the agent program may be employed to distribute the agent and program various computing devices.

In view of all of the foregoing, it will be recognized that the herein described applications (e.g., the client-side activity tracking application and the network-side activity tracking application) improve the functioning of an activity tracking system 100 including one or more of an activity tracking device 20, an electronic display device 30, and a remote system server 40, respectively, or in combination. The improved activity tracking system and related components enable improved training by implementation of training plans with unique scheduling and display of workouts within each training plan, including improved graphical user interfaces that allow users of the system to more easily implement and achieve their training goals. As discussed above, the methods described herein improve upon the functioning of activity tracking systems and their associated devices by providing users with graphical user interfaces for electronic devices that may be used before, during and after a workout to improve achievement of user goals. Prior to a workout, the system provides the user with the ability to configure unique training plans that are individualized to the user and include customized scheduled workouts and associated reminders provided via the system. During workouts, the system provides the user with improved graphical user interfaces that assist the user in achieving micro-level/short-term workout goals. By consistently achieving micro-level workout goals, the user is thereby better equipped to achieve macro-level/long-range workout goals. After a workout, the user is equipped to review performance metrics from each workout, determine whether workout goals were met, and review future workouts within the training plan.

The foregoing detailed description of one or more exemplary embodiments of the fitness tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

What is claimed is:

1. A method of providing workout training for a user of an activity tracking system including a sensor configured to send activity data to at least one personal electronic device, the method comprising:

displaying a plurality of training plan options to the user on a screen of the at least one personal electronic device, each of the training plan options associated with a different user goal and including a plurality of different types of workouts to be performed during a training period;

receiving a selected training plan option from the user via the at least one personal electronic device;

displaying workout day options to the user on the screen, each of a first plurality of the workout day options including a day on which the user intends to workout during each week of the training period for the selected training plan option;

receiving selected workout day options from the user via the at least one personal electronic device;

generating a training schedule for the user based on the selected training plan option and the selected workout day options, wherein the training schedule includes scheduled workout days, one of the plurality of different types of workouts for each scheduled workout day, and a workout goal associated with each scheduled workout day;

displaying one or more reminders on the screen of the at least one personal electronic device on each of the scheduled workout days, each of the reminders including an option to accept or reject a workout;

when the user selects the option to accept the workout on a scheduled workout day, displaying the workout goal associated with the scheduled workout to the user on the screen of the at least one personal electronic device, receiving workout data from the sensor during the workout, determining progress toward the workout goal based on the received workout data, and displaying an indicator of progress toward the workout goal to the user on the screen during the workout, wherein the workout data includes pace data and cadence data, wherein the screen further displays the cadence data for the user on a segmented bar, wherein the segmented bar is segmented into three sections including a first portion associated with cadence data that is within a target range, a second portion associated with cadence data that is below the target range, and a third portion associated with cadence data that is above the target range, wherein a first indicia separates the first portion of the segmented bar from the second portion of the segmented bar, wherein a second indicia separates the first portion of the segmented bar from the third portion of the segmented bar, and wherein a lower value of the target range is displayed in association with the first indicia and an upper value of the target range is displayed in association with the second indicia;

dynamically adjusting the target range and the associated upper value and lower value displayed on the screen during the workout based on changes in the pace data during the workout; and when the user reaches the workout goal, indicating on the screen that the user has reached the workout goal for the workout.

2. The method of claim 1 wherein the types of workouts include at least one long run and at least one segmented test run, wherein workout goals for the scheduled workout days are modified based on the received workout data.

3. The method of claim 1 wherein the workout day options further include an option to identify one day of the week as a scheduled workout day for a particular type of workout.

4. The method of claim 3 wherein the particular type of workout is a long run workout having a distance that is significantly greater than any other workouts for the week.

5. The method of claim 1 further comprising, after the user reaches the workout goal, displaying the training schedule to the user with an indication that the user achieved the workout goal on the scheduled workout day.

6. The method of claim 1 wherein the at least one personal electronic device includes a smartphone and a watch, wherein the screen of the at least one personal electronic device is at least one of: a phone screen of the smartphone and a screen of the watch provided on a watch face.

7. The method of claim 6 wherein the workout goal is at least one of a run duration, a run distance, or a run pace, and the workout goal is represented on the watch face during the workout.

8. The method of claim 7 wherein displaying the indicator of progress toward the workout goal includes displaying an arced bar indicative of the workout goal on the watch face and moving an amount of fill within the arced bar to indicate progress toward the workout goal, wherein the arced bar is completely filled when the user has reached the workout goal for the workout.

9. The method of claim 6 wherein the segmented bar is a segmented arced bar, wherein the first indicia is a first break separating the first portion of the segmented arced bar from the second portion of the segmented arced bar, wherein the second indicia is a second break separating the first portion of the segmented arced bar from the third portion of the segmented arced bar, and wherein the lower value of the target range is displayed on the watch face in proximity of the first break and the upper value of the target range is displayed on the watch face in proximity of the second break.

10. The method of claim 6 wherein the sensor is one of a plurality of shoes sold by a vendor, each of the plurality of shoes including an upper having a unique color different from other of the plurality of shoes, the method further comprising, prior to the workout, pairing the shoe with the watch or the smartphone and displaying a pairing screen to the user with a background color that is the same as the unique color of the upper of the paired shoe.

11. The method of claim 10 wherein the pairing screen displays a pictorial representation of the shoe and a distance logged by the shoe by the activity tracking system.

12. The method of claim 1 wherein the plurality of training plan options are organized by a menu of categories when displayed on the screen, wherein the categories on the menu include race plans, weight-loss plans, and learning-to-run plans.

13. The method of claim 1 wherein the first plurality of workout day options displayed to the user on the screen includes a list of days in a week and an option to select each day of the week as a workout day option, and wherein each of the reminders further identifies the one of the plurality of different types of workouts for the scheduled workout day.

14. An activity tracking system comprising:

a shoe configured to generate activity data and transmit the activity data; and at least one personal electronic device configured to receive the activity data from the shoe, the at least one personal electronic device including at least a smartphone and a watch, each personal electronic device including a memory configured to store the received activity data, a data processor in communication with the memory, and a display in communication with the data processor, the at least one personal electronic device being configured to:

present a plurality of training plan options to a user via the display of the at least one personal electronic device, each of the training plan options associated with a different user goal and including a plurality of different types of workouts to be performed during a training period;

receive a selected training plan option from the user via the display;

present workout day options to the user via the display, each of a first plurality of the workout day options including a day on which the user intends to workout during each week of the training period for the selected training plan option;

receive selected workout day options from the user via the display;

generate a training schedule for the user based on the selected training plan option and the selected workout day options, wherein the training schedule includes scheduled workout days, one of the plurality of different types of workouts for each scheduled workout day, and a workout goal associated with each scheduled workout day;

present one or more reminders to the user on the display on each of the scheduled workout days, each of the reminders including an option to accept or reject a workout;

when the user selects the option to accept the workout on a scheduled workout day, present the workout goal associated with the scheduled workout to the user on the display of the at least one personal electronic device, receive workout data from the shoe during the workout, determine progress toward the workout goal based on the received workout data, and present the progress toward the workout goal to the user on the display during the workout; and display cadence data for the user on a bar on a screen of the watch during the workout, the bar indicating a target cadence range based on a pace of the user during the workout, wherein the watch is further configured to dynamically adjust the target cadence range based on changes in the pace data during the workout.

15. The activity tracking system of claim 14 wherein the plurality of training plan options are presented to the user on a screen of the smartphone, wherein the one or more reminders are presented on the face of the watch, and wherein progress toward the workout goal is presented to the user on the watch face.

16. The activity tracking system of claim 15, wherein a first break separates the first portion of the bar from the second portion of the bar, wherein a second break separates the first portion of the bar from the third portion of the bar, wherein a lower value of the target range is displayed on the watch face in proximity of the first break and an upper value of the target range is displayed on the watch face in proximity of the second break, and wherein the watch is configured to dynamically adjust the target range and the associated upper value and lower value displayed on the watch face during the workout based on changes in the pace data.

17. A non-transitory computer readable medium comprising a plurality of instructions which are configured to, when executed:
cause a plurality of training plan options to be displayed on a screen of at least one personal electronic device, each of the training plan options associated with a different user goal and including a plurality of different types of workouts to be performed during a training period;
receive a selected training plan option from a user via the at least one personal electronic device;
cause workout day options to be displayed on the screen, each of a first plurality of the workout day options including a day on which the user intends to workout during each week of the training period for the selected training plan option;
receive selected workout day options from the user via the at least one personal electronic device;
generate a training schedule for the user based on the selected training plan option and the selected workout day options, wherein the training schedule includes scheduled workout days, one of the plurality of different types of workouts for each scheduled workout day, and a workout goal associated with each scheduled workout day;
cause one or more reminders to be displayed on the screen of the at least one personal electronic device on each of the scheduled workout days, each of the reminders including an option to accept or reject a workout;
when the user selects the option to accept the workout on a scheduled workout day, cause the workout goal associated with the scheduled workout to be displayed on the screen of the at least one personal electronic device, receive workout data from the sensor during the workout, determine progress toward the workout goal based on the received workout data, and cause an indicator of progress toward the workout goal to be displayed on the screen during the workout;
display cadence data for the user on a segmented bar on the screen during the workout, the segmented bar including a first portion associated with cadence data that is within a target range, a second portion associated with cadence data that is below the target range, and a third portion associated with cadence data that is above the target range, wherein a first break separates the first portion of the bar from the second portion of the bar, wherein a second break separates the first portion of the bar from the third portion of the bar, wherein a lower value of the target range is displayed on the watch face in proximity of the first break and an upper value of the target range is displayed on the watch face in proximity of the second break, and wherein the watch is configured to dynamically adjust the target range and the associated upper value and lower value displayed on the screen during the workout based on changes in the pace data during the workout; and
when the user reaches the workout goal, cause an indicator to be displayed on the screen showing that the user has reached the workout goal for the workout.

18. The non-transitory computer readable medium of claim 17 wherein the workout day options further include an option to identify one day of the week as a scheduled workout day for a long run workout having a distance that is significantly greater than any other workouts for the week.

* * * * *